(12) United States Patent
Ohnogi et al.

(10) Patent No.: US 7,078,386 B2
(45) Date of Patent: Jul. 18, 2006

(54) ENHANCING AGENT FOR NERVE GROWTH FACTOR PRODUCTION COMPRISING A COMPOUND HAVING A COUMARIN BACKBONE OR A COMPOUND HAVING A 2-DIMETHYL CHROMAN BACKBONE

(75) Inventors: Hiromu Ohnogi, Kusatsu (JP); Masahiro Shiraga, Otsu (JP); Hiroaki Sagawa, Kusatsu (JP); Ikunoshin Kato, Uji (JP)

(73) Assignee: Takara Bio, Inc., Otsu (JP)

( * ) Notice: Subject to any disclaimer, the term of this patent is extended or adjusted under 35 U.S.C. 154(b) by 152 days.

(21) Appl. No.: 10/474,708

(22) PCT Filed: Mar. 28, 2002

(86) PCT No.: PCT/JP02/03037

§ 371 (c)(1),
(2), (4) Date: Oct. 10, 2003

(87) PCT Pub. No.: WO02/083660

PCT Pub. Date: Oct. 24, 2002

(65) Prior Publication Data

US 2004/0122082 A1  Jun. 24, 2004

(30) Foreign Application Priority Data

Apr. 10, 2001 (JP) ............................. 2001-111932

(51) Int. Cl.
*A61K 31/70* (2006.01)
*A23L 2/00* (2006.01)
*C07H 15/24* (2006.01)
*C07D 311/00* (2006.01)

(52) U.S. Cl. ................. 514/25; 426/321; 426/534; 426/590; 426/599; 536/18.1; 549/275

(58) Field of Classification Search ............. 514/25; 426/321, 534, 590, 599; 536/18.1; 549/275
See application file for complete search history.

(56) References Cited

U.S. PATENT DOCUMENTS 5,639,737 A * 6/1997 Rubin ..................... 514/53
5,641,789 A * 6/1997 Marfat .................... 514/314
6,475,544 B1 * 11/2002 Hiramoto et al. .......... 426/321

FOREIGN PATENT DOCUMENTS

| CN | 1163760 A | 11/1997 |
|---|---|---|
| EP | 0 515 917 B1 | 12/1992 |
| EP | 1 277 473 A1 | 1/2003 |
| EP | 1 283 037 A1 | 2/2003 |
| JP | 4-210643 A | 7/1992 |

OTHER PUBLICATIONS

Robert D. Terry et al.; Ann. Rev. Neurosci., 1980 vol. 3, pp. 77-95.
S. Korsching et al.; The EMBO Journal, vol. 4, No. 6, pp. 1389-1393, 1985.
Jean L. Marx, Science, vol. 232, Jun. 13, 1986, pp. 1341-1342.
Franz Hefti; The Journal of Neuroscience, Aug. 1986, No. 6(8), pp. 2155-2162.
F. Hefti et al.; Brain Research, vol. 293, 1984, pp. 305-311.
Lawrence F. Kromer; Science, vol. 235, Jan. 9, 1987, pp. 214-216.
Lawrence R. Williams et al.; Proc. Natl. Accad. Sci., vol. 83, pp. 9231-9235, Dec. 1986, pp. 9231-9235.
Yoshiko Furukawa et al.; The Journal of Biological Chemistry; vol. 259, No. 2, Issue of Jan. 25, 1984; pp. 1259-1264.
Shoei Furukawa et al.; Biochemical and Biophysical Research Communications; vol. 136, No. 1, Apr. 14, 1986, pp. 57-63.
Yoshiko Furukawa et al.; The Journal of BIological Chemistry; vol. 261, No. 13, Issue of May 5, 1986, pp. 6039-6047.
Murase Katsuhito et al, *Biosci. Biotech. Biochem.*, 58(5), 900-905, 1994.
Velasco Lara et al., *Eur. J. Biochem.*, 268, 531-535 (2001).

* cited by examiner

*Primary Examiner*—Elli Peselev
(74) *Attorney, Agent, or Firm*—Birch, Stewart, Kolasch & Birch, LLP

(57) ABSTRACT

The present invention relates to a medicament, a food, a beverage or a feed, each comprising as an effective ingredient a compound having an enhancing action for NGF production, which is effective for a treatment, an amelioration of symptom, prevention or the like of a disease requiring enhancement of NGF production, wherein the compound has a coumarin and/or chroman backbone. Since no toxicity is especially found in the effective ingredient of the present invention, and there is no risk of incidence of adverse actions, the treatment or the like of the above disease can be safely and appropriately carried out.

12 Claims, 14 Drawing Sheets

ENHANCING AGENT FOR NERVE GROWTH FACTOR PRODUCTION COMPRISING A COMPOUND HAVING A COUMARIN BACKBONE OR A COMPOUND HAVING A 2-DIMETHYL CHROMAN BACKBONE

This application is the national phase under 35 U.S.C. § 371 of PCT International Application No. PCT/JP02/03037 which has an International filing date of Mar. 28, 2002, which designated the United States of America.

TECHNICAL FIELD

The present invention relates to a medicament, a food, a beverage or a feed, each utilizing an enhancing action for nerve growth factor of a compound having a coumarin and/or chroman backbone.

BACKGROUND ART

Nerve cells play a principal role for sustaining psycho-activities of human being such as intellectual functions, memory, emotions and behaviors. It has been thought that the differentiation, survival and exhibition of functions of the nerve cells which are the foundations of these psycho-activities need a neurotrophic factor specific for each nerve cell. Among the neurotrophic factors, one of which existence and function have been firstly elucidated is a nerve growth factor (hereinafter simply referred to as "NGF"), and currently, there have been found a brain-derived-neurotrophic factor, neurotrophin-3, neurotrophin-4/5, and the like.

NGF is a neurotrophic factor of a large cellular cholinergic nerve cell of basal portion of the forebrain, so that its association with Alzheimer's dementia has been remarked [*Pharmacia*, Vol. 22, No. 2, 147–151 (1986), Ronen Seishin Igaku (*Senile Psychiatry*), Vol. 3, No. 6, 751–758 (1986)].

Alzheimer's dementia refers to a disease that gives a pathological finding such as senile plaque or Alzheimer's fibrillar changes, which are accompanied by a clinical picture such as developmental disability, manic state, tonic seizures of lower limbs, or epileptic seizure, and is one disease of senile dementia. The Alzheimer's dementia tends to be increasing in recent aging society, so that a larger societal interest has been drawn thereto. However, there has not yet been found a method for ameliorating or treating such symptoms. Also, as to juvenile Alzheimer's dementia, there has not yet been found a method for ameliorating or treating such symptoms.

In the brain of a patient with Alzheimer's dementia, there has been found a dramatic denaturation, a drastic lowering of the activity of choline acetyl transferase (CAT), in the basal portion of the forebrain centering about Meynert's basal nuclei [*Annu. Rev. Neurosci.*, Vol. 3, 77 (1980)]. In the studies of a rat brain in 1985, there has been elucidated that NGF is a neurotrophic factor at this site of the brain [*EMBO J.*, Vol. 4, 1389 (1985)], so that the association of NGF with this disease has been remarked. In addition, there have been elucidated that in the striate body of the brain of a patient with Huntington's chorea, there are remarkable detachment of GABAergic nerve cell as well as detachment of cholinergic nerve cell, so that NGF also acts on the endogenous cholinergic nerve cell of the striate body [*Science*, Vol. 232, 1341 (1986)], addressing a possibility that this disease is associated with NGF. The effects of NGF have been studied with an animal such as a rat which can serve as a model for various nerve diseases. There has been reported that the degeneration of the nerve cell can be stopped in a rat if NGF is intracerebrally administered before the degeneration becomes remarkable, and that if so, the lowering of CAT activity is also prevented [*J. Neurosci.*, Vol. 6, 2155 (1986), Brain Res., Vol. 293, 305 (1984), *Science*, Vol. 235, 214 (1987), *Proc. Natl. Acad. Sci. USA*, Vol. 83, 9231 (1986)]. Also, it has been proven that NGF is biosynthesized in the peripheral sympathetic nerve-dominant tissues and in the brain, and that each of fibroblasts or astroglia which are interstitial cells for peripheral tissues or brain tissues plays an important role for the NGF biosynthesis [*J. Biol. Chem.*, Vol. 259, 1259 (1984), *Biochem. Biophys. Res. Commun.*, Vol. 136, 57 (1986)]. In addition, it has been elucidated that antigenicity, molecular weight, isoelectric point and biological activity of the fibroblast-producing or astroglia-producing NGF are the same as NGF of conventionally well studied submandibular gland. At the same time, it has been found that a catecholamine such as norepinephrine, epinephrine or dopamine shows enhancing action for NGF production by a test of adding various neurotransmitters to a culture medium of fibroblasts (L-M cells) and astroglia [*J. Biol. Chem.*, Vol. 261, 6039 (1986)].

As described above, there has been expected that NGF can be used as a therapeutic agent for stopping degeneration in these nerve diseases in which a site at which NGF acts as a neurotrophic factor is degenerated. In addition, once the cranial nerve cells are degenerated by cebrovascular disorders, cerebral tumor, cerebral apicitus, head injury, nerve degenerative disease, intoxication with an anesthetic, or the like, the degenerated cranial nerve cells would never recover during the life time, whereby various disorders such as emotional disorders and behavioral abnormality are consequently caused in addition to lowering in the intellectual functions and memory disabilities. On the other hand, nerve fiber shows plasticity, that is, when the nerve fiber is damaged, budding takes place from its surrounding healthy fibers, so that a new synapsis is formed in place of the damaged synapsis. Therefore, it has been expected that NGF can be used as a therapeutic agent for promoting restoration and regeneration of nerve functions at this stage.

However, when NGF is applied to a treatment of various nerve diseases, NGF must reach in very close vicinity of nerve cell that requires NGF, and NGF must be transmitted to lesion site of the cranial cell in a case of a disease in the central nervous system. However, NGF cannot be transmitted into the brain through the blood system. This is because the vascular endothelial cells in the brain are bound to each other by adhesion bonding (referred to as brain blood barrier), so that there is a limitation in the transport of a substance other than water, gas or an oil-soluble substance from blood to a brain tissue, whereby a protein (including NGF), which is polymeric substance, cannot pass through the brain blood barrier. There is a too large risk involved in the introduction of NGF directly into the brain by a surgical means, even if the introduction is conducted by the current techniques.

On the other hand, there has been developed a substance for enhancing NGF production, not a direct administration of NGF. Most of the compounds, however, have various problems such that the compounds have strong toxicity, or the compounds have effective concentration very closely approximating concentration at which toxicity is shown, or the compounds have severe adverse actions against nervous system such as nerve excitation action. Therefore, these compounds have not yet been actually used.

DISCLOSURE OF INVENTION

An object of the present invention is to provide a medicament, a food, a beverage or a feed, each comprising as an effective ingredient a compound having an enhancing action for NGF production, which is effective for a treatment, an amelioration of symptom, prevention or the like of a disease requiring enhancement of NGF production.

As a result of intensive studies, the present inventors found that a compound having a coumarin and/or chroman backbone has an enhancing activity for NGF production, and completed the present invention.

Concretely, summarizing the present invention, a first invention of the present invention relates to a therapeutic agent or prophylactic agent for a disease requiring enhancement of nerve growth factor production (in some cases referred to herein as a medicament), characterized in that the therapeutic agent or prophylactic agent comprises as an effective ingredient at least one compound selected from the group consisting of (A) a compound having a coumarin backbone, (B) a compound having a 2-dimethyl chroman backbone and pharmacologically acceptable salts thereof.

In the first invention of the present invention, the compound having a coumarin backbone is exemplified by a compound represented by the general formula (I):

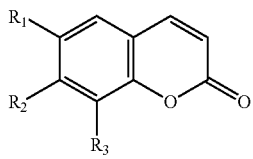

(I)

wherein each of $R_1$, $R_2$ and $R_3$ is hydrogen atom, hydroxyl group, an aliphatic group, an aromatic group, an aromatic-aliphatic group or a saccharide residue, which may be identical or different, or
a compound represented by the general formula (II):

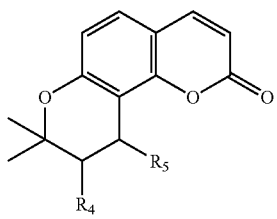

(II)

wherein each of $R_4$ and $R_5$ is hydrogen atom, hydroxyl group, an $R_iO$ group, an $R_{ii}COO$ group, or a saccharide residue, which may be identical or different.

In addition, the compound represented by the general formula (I) is especially preferably exemplified by
7-O-β-D-glucopyranosyloxy-8-prenyl coumarin or
7-β-D-glucopyranosyloxy-6-prenyl coumarin, and the compound represented by the general formula (II) is especially preferably exemplified by
3'-O-β-D-glucopyranoyl khellactone or
4'-O-angeloyl-3'-O-[6-O-(β-D-glucopyranosyl)-β-D-glucopyranosyl]-khellactone.

In the first invention of the present invention, the compound having a 2-dimethyl chroman backbone is exemplified by a compound represented by the general formula (III):

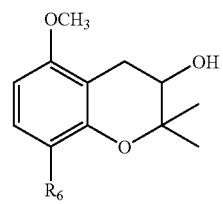

(III)

wherein $R_6$ is hydrogen atom, hydroxyl group, carboxyl group, an aliphatic group, an aromatic group, an aromatic-aliphatic group or a saccharide residue.

In addition, the compound represented by the general formula (III) is especially preferably exemplified by
8-carboxyl-3-hydroxy-5-methoxy-2-dimethyl chroman or
3-hydroxy-8-[3-(4-hydroxyphenyl)-acryloyl]-5-methoxy-2-dimethyl chroman.

The second and third inventions of the present invention relate to an enhancing agent for NGF production, and a food, a beverage or feed for enhancing NGF production, characterized in that each comprises the same effective ingredient as that of the first invention of the present invention.

BEST MODE FOR CARRYING OUT THE INVENTION

Figure 1:
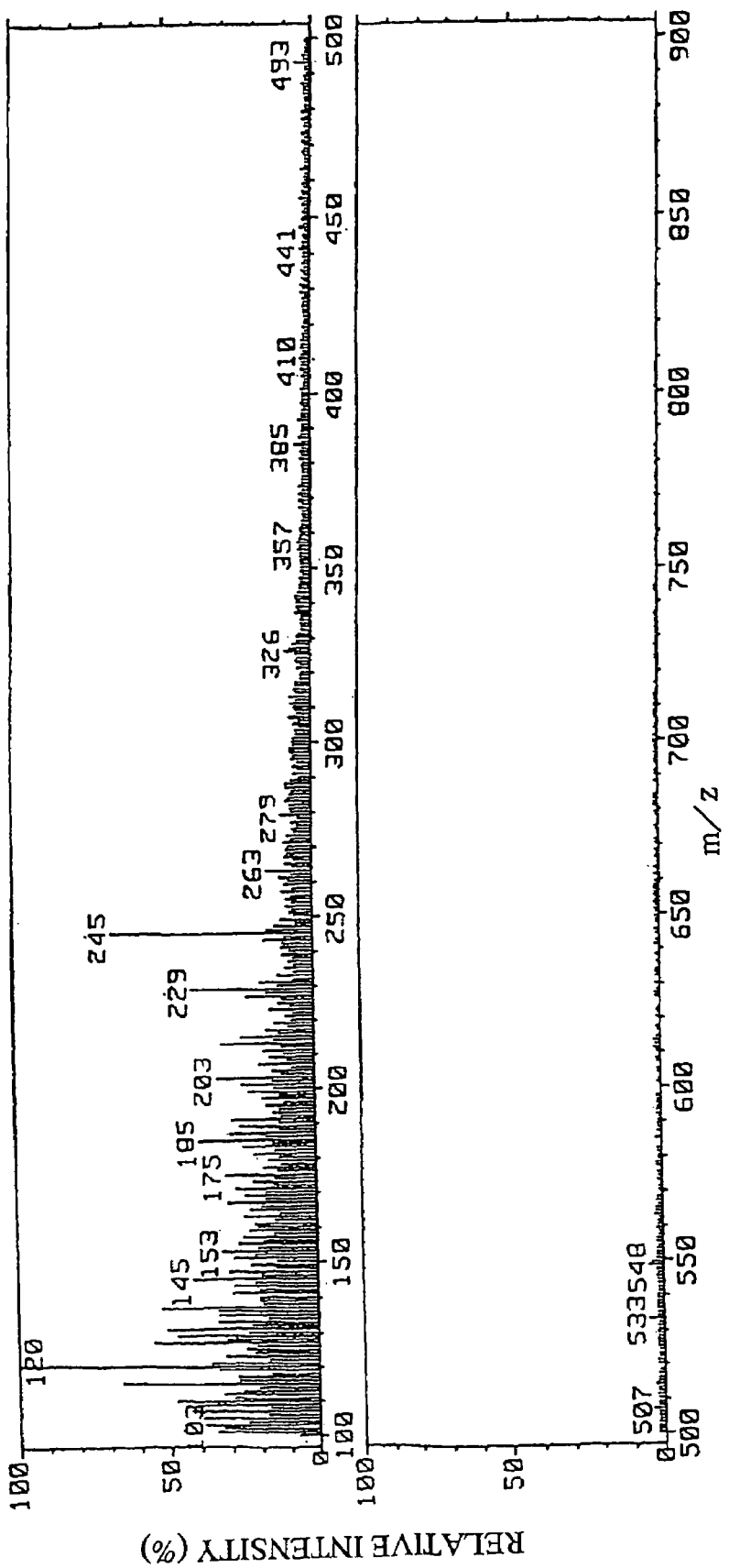
FIG. 1 is a chart showing FAB-MS spectrum of the fraction 10 from root portions of Angelica keiskei koidz.

The term "enhancing action for NGF production" and "enhancing activity for NGF production" as used herein each refers to enhancement of NGF production and a function for enhancing NGF production, and is not intended to particularly strictly distinguish in its meaning. In addition, the term "enhance" encompasses an embodiment in which the amount of the desired substance is increased after the action as compared to that before the action of the effective ingredient of the present invention, as well as an embodiment (induction) in which the desired substance is produced by the action of the effective ingredient of the present invention. In addition, any of the substances listed as the effective ingredient in the present specification can be used alone or in admixture of two or more kinds in the present invention.

The compound which is used as the effective ingredient in the present invention is at least one compound selected from the group consisting of (A) a compound having a coumarin backbone, (B) a compound having a 2-dimethyl chroman backbone and pharmacologically acceptable salts thereof (hereinafter also referred to as a "compound which is usable in the present invention" in some cases). The compound is not particularly limited as long as the compound has an enhancing activity for NGF production. Also, as described below, the compound may be a derivative of the compound which can function as a prodrug. Therefore, the effective ingredient of the present invention encompasses the above-mentioned compounds (A) and (B), derivatives of the above-mentioned compounds (A) and (B) as long as the desired effects of the present invention can be obtained, and pharmacologically acceptable salts thereof. The phrase "pharmacologically acceptable" as used herein means that the compound is substantially nontoxic against an organism. Also, various isomers such as optical isomers, keto-enol tautomers, and geometric isomers of the above-mentioned compounds (A) and (B) can be all used in the present invention, alone or in admixture of each of isomers, as long as these isomers have an enhancing activity for NGF production.

In the present invention, the compound having a coumarin backbone is not particularly limited, and is, for instance, exemplified by the compound represented by the above-mentioned general formula (I) or (II).

On the other hand, the compound having a 2-dimethyl chroman backbone is not particularly limited, and is, for instance, exemplified by the compound represented by the above-mentioned general formula (III).

The aliphatic group as referred to herein includes, for instance, linear alkyl groups having 1 to 30 carbon atoms, such as methyl group, ethyl group and n-propyl group; branched alkyl groups such as isopropyl group, isobutyl group, sec-butyl group, tert-butyl group, isopentyl group, neopentyl group and tert-pentyl group; linear alkenyl groups such as ethenyl group, allyl group, trans-1-propenyl group, cis-1-propenyl group, cis-8-heptadecenyl group, cis-8-cis-11-heptadecadienyl group, cis-8-cis-11-cis-14-heptadecatrienyl group, cis-5-cis-8-cis-11-heptadecatrienyl group, cis-4-cis-7-cis-10-nonadecatrienyl group, cis-4-cis-7-cis-10-cis-13-nonadecatetraenyl group, cis-4-cis-7-cis-10-cis-13-cis-16-nonadecaheptenyl group, cis-12-heneicosenyl group, and cis-3-cis-6-cis-9-cis-12-cis-15-cis-18-heneicohexaenyl group; and branched alkenyl groups such as prenyl group, isopropenyl group, cis-1-methyl-1-propenyl group, trans-1-methyl-1-propenyl group, trans-1-methyl-1-propenyl group and trans-1-ethyl-1-propenyl group. The preferred example of the aliphatic group includes prenyl group from the viewpoint of exhibiting the desired effects of the present invention.

Also, the aromatic group includes, for instance, phenyl group, naphthyl group, biphenyl group, pyrolyl group, pyridyl group, indolyl group, imidazolyl group, tolyl group, xylyl group and the like.

As the preferred examples of the aromatic-aliphatic group, there may be exemplified saturated or unsaturated aromatic-aliphatic group having 1 to 20 carbon atoms, especially preferably 3-(4-hydroxyphenyl)-acryloyl group. Besides them, for instance, the aromatic-aliphatic group includes a phenylalkyl group of which alkyl group has 1 to 20 carbon atoms (for instance, benzyl group, phenetyl group), styryl group, cinnamyl group and the like.

The sugar constituting the saccharide residue includes, for instance, monosaccharides such as glucose, threose, ribose, apiose, allose, ramnose, arabinopyranose, ribulose, xylose, galactose, mannose, talose, fucose, fructose, glucuronic acid and galacturonic acid; disaccharides such as gentiobiose, neohesperidose, lutinose, agarobiose, isomaltose, sucrose, xylobiose, nigerose, maltose and lactose, oligosaccharides derived from polysaccharides such as agarose and fucoidan, polysaccharides such as agarose and fucoidan, or the like. Preferred examples of the sugar include glucose and gentiobiose, from the viewpoint of exhibiting the desired effects of the present invention. In addition, the sugar residue includes compounds in which a sugar is bonded to a carbon other than that of the reducing end of the saccharide via C—C bonding, as well as compounds in which a sugar is bonded via O—, N—, S— or C-glycoside bonding.

As $R_i$ for the $R_iO$ group, there are exemplified the aliphatic groups and the aromatic groups given above.

In addition, as $R_{ii}$ for the $R_{ii}COO$ group, there are exemplified the aliphatic groups and the aromatic groups given above. A preferred example of the $R_{ii}COO$ group includes angeloyl group, from the viewpoint of exhibiting the desired effects of the present invention.

Furthermore, the compounds represented by the general formulas (I), (II) and (III) usable in the present invention can be formed into a derivative (prodrug), which can be readily hydrolyzed in the body to exhibit the desired effects by, for instance, subjecting the compound to esterification. The prodrug may be prepared in accordance with a known method (see *Pharmaceutical Research and Development*, Vol. 7, Drug Design p. 163–198, HIROKAWA Publishing Co.). Here, the derivative may be their salts.

An especially preferred example of the above-mentioned compound represented by the general formula (I) includes, for instance, 7-O-β-D-glucopyranosyloxy-8-prenyl coumarin or 7-β-D-glucopyranosyloxy-6-prenyl coumarin. Also, a preferred example of the above-mentioned compound represented by the general formula (II) includes, for instance, 3'-O-β-D-glucopyranoyl khellactone or 4'-O-angeloyl-3'-O-[6-O-(β-D-glucopyranosyl)-β-D-glucopyranosyl]-khellactone. The structural formulas of these compounds are sequentially given in the following formulas (IV) to (VII).

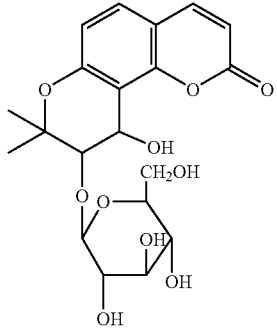
(IV)

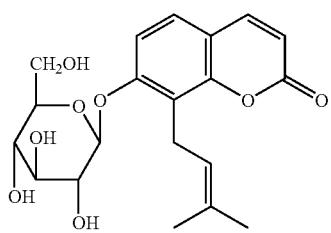
(V)

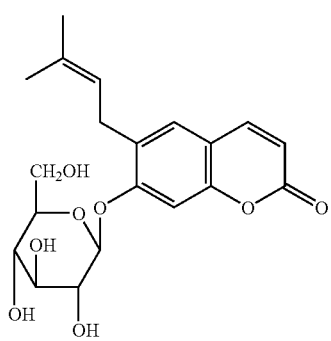
(VI)

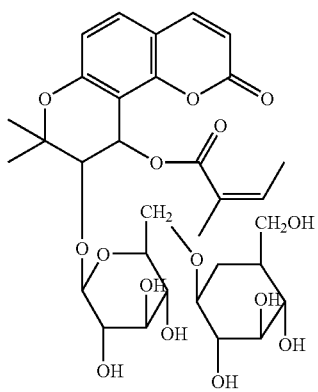
(VII)

In addition, a preferred example of the above-mentioned compound represented by the general formula (III) includes, for instance, 8-carboxyl-3-hydroxy-5-methoxy-2-dimethyl chroman or 3-hydroxy-8-[3-(4-hydroxyphenyl)-acryloyl]-5-methoxy-2-dimethyl chroman.

For instance, the structural formula of the former compound is shown in the following formula (VIII).

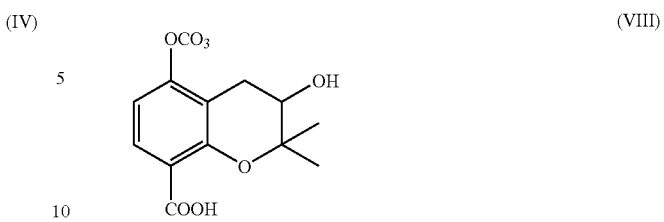
(VIII)

As mentioned above, any of the effective ingredient of the present invention as described above has an enhancing action for NGF production. The exhibition of the action can be evaluated by, for instance, the method shown in item (2) of Example 1 set forth below.

When the compound usable as the effective ingredient in the present invention exists as a natural product, the compound can be obtained by extracting from a plant (for instance, a plant belonging to Umbelliferae such as *Angelica keiskei* koidz.) and purifying the extract in accordance with an ordinary method. The extraction can be carried out by a known method. For instance, the raw material is powdered or cut into thin pieces, and thereafter extracted in a batch process or continuous process using a solvent. The extraction solvent includes, for instance, hydrophilic or lipophilic solvents such as water, chloroform, alcohols such as ethanol, methanol and isopropyl alcohol, ketones such as acetone and methyl ethyl ketone, methyl acetate, and ethyl acetate, which can be used alone or as a mixed solution. The extraction temperature may be appropriately set as occasion demands, and the extraction procedures may be repeated several times as occasion demands. Purification of the extract can be carried out by fractionating and purifying the extract using various chromatographies and the like.

In other words, for instance, when the compound usable in the present invention is purified from *Angelica keiskei* koidz., the compound usable in the present invention can be obtained by subjecting root portions of *Angelica keiskei* koidz. to extraction procedures with water as a solvent, and thereafter fractionating and purifying the resulting extract by reverse phase chromatography.

The above-mentioned 7-β-D-glucopyranosyloxy-6-prenyl coumarin, 4'-O-angeloyl-3'-O-[6-O-(β-D-glucopyranosyl)-β-D-glucopyranosyl]-khellactone and 8-carboxyl-3-hydroxy-5-methoxy-2-dimethyl chroman are compounds which are isolated from *Angelica keiskei* koidz. for the first time in the present invention, of which enhancing actions for NGF production have been also confirmed for the first time. The present invention also encompasses these compounds.

Here, as the compound which can be used as the effective ingredient in the present invention, there can be utilized, for instance, commercially available compounds as long as they have enhancing activities for NGF production, or there can be appropriately prepared by a known method using ortho-coumaric acid as a starting raw material (see *Bull. Soc.*, p 2929 (1971)). Alternatively, the compound can be appropriately prepared from the reaction of diketene with phenol (see *J. Chem. Soc.*, p. 854 (1954)).

The salts of various kinds of the above-mentioned compounds usable in the present invention include, for instance, alkali metal salts, alkaline earth metal salts, salts with an organic base, and the like. The salts include, for instance, salts with sodium, potassium, calcium, magnesium, ammonium or protonated benzathine (N,N'-di-benzylethylenediamine), choline, ethanolamine, diethanolamine, ethylenediamine, meglamine (N-methylglucamine), benethamine (N-benzylphenetylamine), piperazine or tolomethamine (2-amino-2-hydroxymethyl-1,3-propanediol).

NGF is an endogenous growth factor for maintaining viability and functions of nerve cells, elongating nerve cells in accordance with a concentration gradient of NGF, or the like. By enhancing the production of NGF, the treatment or prevention of senile dementia such as Alzheimer's disease, peripheral nerve disorder, cerebrovascular disorder, cerebral tumor, cerebral apicitis, nerve degenerative disease caused by head injury, diseases requiring recovery and regeneration of nerve functions, caused by intoxication with an anesthetic, and the like could be carried out. In addition, it is considered to be useful in the treatment or prevention of amyotrophic lateral sclerosis, drug-induced peripheral nerve disorder, diabetic peripheral nerve disorder, Parkinson's disease, sensory nerve disorder, retinitis pigmentosa, macular dystrophy, and the like. The effective ingredient of the present invention has an enhancing action for NGF production. Therefore, the medicament, food, beverage or feed of the present invention each comprising the effective ingredient is especially effective for treatment, amelioration of symptoms, prevention or the like for a disease requiring enhancement for NGF production concretely exemplified above, the disease not being particularly limited as long as the disease can be treated or prevented by the enhancement of NGF production. In addition, the effective ingredient of the present invention is not especially found to be toxic, and there is no risk of the incidence of adverse actions, as mentioned below. Therefore, the enhancement for NGF production can be safely and appropriately carried out. This is an important advantage for the medicament, food, beverage or feed of the present invention.

The therapeutic agent or prophylactic agent of the present invention for a disease requiring enhancement for NGF production includes those formed into a preparation by combining the above-mentioned effective ingredient of the present invention with a known pharmaceutical carrier. In the embodiment of the present invention, a pharmacologically acceptable salt is used as the salt which is the effective ingredient.

The therapeutic agent or prophylactic agent of the present invention is usually manufactured by formulating the above-mentioned effective ingredient with a pharmacologically acceptable liquid or solid vehicle. During the manufacture, a solvent, a dispersant, an emulsifier, a buffer, a stabilizer, an excipient, a binder, a disintegrant, a lubricant, or the like is optionally added thereto, so that a solid agent such as a tablet, a granule, a powder, a fine powder, and a capsule, or a liquid agent such as a common liquid agent, a suspension agent or an emulsion agent can be formed. In addition, there can be also made into a dry product which can be made liquid by adding an appropriate liquid vehicle before use, and an external preparation.

The pharmaceutical carrier can be selected depending upon the administration form and preparation form of the therapeutic agent or prophylactic agent. In the case of an orally administered preparation comprising a solid composition, the preparation can be produced in the form of a tablet, a pill, a capsule, a powder, a fine powder, a granule or the like. There can be utilized, for instance, starch, lactose, saccharose, mannitol, carboxymethyl cellulose, cornstarch, an inorganic salt or the like. In addition, during the preparation of the orally administered preparation, a binder, a disintegrant, a surfactant, a lubricant, a fluidity accelerator, a flavor, a colorant, a perfume, and the like can be further formulated. In the case of forming into a tablet or pill, for instance, the tablet or pill may be covered with a sugar-coating made of sucrose, gelatin or hydroxypropyl cellulose, or with a film made of a substance soluble in the stomach or intestine as occasion demands. In the case of an orally administered preparation comprising a liquid composition, the preparation can be prepared in the form of a pharmaceutically acceptable emulsion, solution, suspension, syrup, or the like. In this case, for instance, purified water, ethanol or the like is utilized as a carrier. Furthermore, an auxiliary agent such as a wetting agent or a suspending agent, a sweetener, a flavor, an antiseptic, or the like may be added as desired.

On the other hand, in the case of a non-orally administered preparation, the preparation can be prepared by dissolving or suspending the above-mentioned effective ingredient of the present invention in a diluent such as distilled water for injection, physiological saline, an aqueous solution of glucose, vegetable oil for injection, sesame oil, peanut oil, soybean oil, corn oil, propylene glycol or polyethylene glycol, by a conventional method, and adding a microbicide, a stabilizer, an osmotic regulator, a soothing agent, or the like as necessary. It is also possible to produce a solid composition which is dissolved in sterile water or a sterile solvent for injection before use.

The external preparation includes solid, semi-solid or liquid preparations for percutaneous administration or transmucosal (oral or intranasal) administration. The external preparation also includes suppositories and the like. For instance, the external preparation may be prepared as liquid preparations including emulsions, suspensions such as lotions, external tinctures, and liquid agents for transmucosal administration; ointments including oily ointments and hydrophilic ointments; medical adhesives for percutaneous administration or transmucosal administration such as films, tapes and poultices; and the like.

Each of the above-mentioned various preparations can be appropriately produced by conventional methods by utilizing known pharmaceutical vehicles and the like. The content of the effective ingredient in the preparation is not particularly limited, as long as the content is in an amount so that the effective ingredient can be preferably administered within the dose described below in consideration of administration form, administration method and the like of the preparation.

The therapeutic agent or prophylactic agent of the present invention is administered via an administration route appropriate for each of the preparation form. The administration method is not limited to specific one. The agent can be administered internally or externally (or topically) or by injection. The injection can be administered, for instance, intravenously, intramuscularly, subcutaneously, intracutaneously, or the like. As to an external preparation, a suppository may be administered according to its proper administration method.

The dose of the therapeutic agent or prophylactic agent of the present invention is changeable and properly set depending upon its preparation form, administration method, purpose of use, age, body weight, symptom or the like of a patient to which the therapeutic agent or prophylactic agent is applied, or the like. Generally, the dose of the agent as the dose for adult per day of the above-mentioned effective ingredient contained in the preparation is preferably from 0.1 µg to 200 mg/kg weight. As a matter of course, the dose varies depending upon various conditions, so that an amount smaller than the dose mentioned above may be sufficient, or an amount exceeding the dose range may be required. Administration may be carried out once or in several divided portions in a day within the desired dose range. The therapeutic agent or prophylactic agent of the present invention can be directly orally administered, or the agent can be added to any foodstuffs to take it on a daily basis. The period of administration may be appropriately determined depending upon the exhibition of the desired effects.

In addition, the present invention can provide an enhancing agent for NGF production comprising the above-mentioned effective ingredient. The enhancing agent may be the above-mentioned effective ingredient itself, or a composition comprising the above-mentioned effective ingredient. In the embodiment of the present invention, a pharmacologically acceptable salt is preferable as a salt which is the effective ingredient. The enhancing agent for NGF production may be produced by, for instance, formulating the above-mentioned effective ingredient with other ingredients which can be used for the same application as the effective ingredient, and forming into a form of reagent usually used according to the above-mentioned process for producing the therapeutic agent or prophylactic agent. The content of the above-mentioned effective ingredient in the enhancing agent is not particularly limited, as long as the content is in an amount so that the desired effects of the present invention can be exhibited in consideration of purpose of use, method of use or the like of the enhancing agent. Also, the amount of the enhancing agent used is not particularly limited, as long as the desired effects of the present invention can be exhibited. Especially in the case where the enhancing agent is administered to a living body, the enhancing agent is preferably used in an amount so that the effective ingredient can be administered according to any administration methods within the dose range of the effective ingredient for the above-mentioned therapeutic agent or prophylactic agent. The enhancing agent for NGF production is useful for enhancement of NGF production in a disease requiring enhancement for NGF production. In addition, the enhancing agent is also useful for screening of drugs for diseases associated with NGF. Furthermore, the enhancing agent is useful for functional studies concerning NGF or physical changes in nerve cells.

Further, in a still another embodiment of the present invention, there can be provided a method for enhancing NGF production, comprising administering the above-mentioned effective ingredient according to the present invention to an animal. In the embodiment of the present invention, a pharmacologically acceptable salt is preferred as a salt which is the effective ingredient. This method can be carried out by administering the above-mentioned effective ingredient, preferably as the above-mentioned enhancing agent for NGF production, to an animal that is predicted to require or requires enhancement of NGF production, wherein the NGF production is enhanced by the administration. The administration method, dose, or the like of the effective ingredient may be similar to that of the above-mentioned enhancing agent for NGF production. In the method for enhancing NGF production, the therapeutic agent or prophylactic agent, or the food, beverage or feed described below of the present invention can be also used. In addition, the term "animal" includes a mammal such as human, dogs, cats, Bos, Porcus, Equus, and the like, among which the method is preferably used for human. The method for enhancing NGF production is useful for, for instance, the enhancement of NGF production in a case of treatment or prevention of a disease requiring enhancement for NGF production. In addition, the method is also useful for screening of drugs for diseases associated with NGF. Furthermore, the method is useful for functional studies concerning NGF or physical changes in nerve cells.

In addition, the present invention provides a food, beverage or feed for enhancing NGF production in which the above-mentioned effective ingredient is contained, added and/or diluted. In the embodiment of the present invention, as a salt which is the effective ingredient, a pharmacologically acceptable salt or a salt of the same level of safety thereof can be suitably used. Since the food, beverage or feed of the present invention has enhancing action for NGF production, the food, beverage or feed is very useful in amelioration of symptoms or prevention for a disease requiring enhancement for NGF production.

Here, in the present specification, the term "containing" refers to an embodiment of containing the effective ingredient usable in the present invention in the food, beverage or feed; the term "adding" refers to an embodiment of adding the effective ingredient usable in the present invention to a raw material for the food, beverage or feed; and the term "diluting" refers to an embodiment of adding a raw material for the food, beverage or feed to the effective ingredient usable in the present invention.

The method for preparing the food, beverage or feed of the present invention is not particularly limited. For instance, formulation, cooking, processing, and the like can be carried out in accordance with those generally employed for foods, beverages or feeds, and the food, beverage or feed of the present invention can be prepared by the general methods for preparing a food, beverage or feed, as long as the resulting food, beverage or feed may contain the above-mentioned effective ingredient of the present invention, wherein the effective ingredient has enhancing action for NGF production.

The food or beverage of the present invention is not particularly limited. The food or beverage includes, for instance, processed agricultural and forest products, processed stock raising products, processed marine products and the like, including processed grain products such as processed wheat products, processed starch products, processed premix products, noodles, macaronis, bread, bean jam, buckwheat noodles, wheat-gluten bread, rice noodle, fen-tiao, and packed rice cake; processed fat and oil products such as plastic fat and oil, tempura oil, salad oil, mayonnaise, and dressing; processed soybean products such as tofu products, soybean paste, and fermented soybeans; processed meat products such as ham, bacon, pressed ham, and sausage; marine products such as frozen ground fish, boiled fish paste, tubular roll of boiled fish paste, cake of ground fish, deep-fried patty of fish paste, fish ball, sinew, fish meat ham, sausage, dried bonito, products of processed fish egg, marine cans, and preserved food boiled down in soy sauce (tsukudani); milk products such as raw material milk, cream, yogurt, butter, cheese, condensed milk, powder milk, and ice cream; processed vegetable and fruit products such as paste, jam, pickled vegetables, fruit beverages, vegetable beverages, and mixed beverages; confectioneries such as chocolates, biscuits, sweet bun, cake, rice cake snacks and rice snacks; alcohol beverages such as sake, Chinese liquor, wine, whiskey, Japanese distilled liquor (shochu), vodka, brandy, gin, rum, beer, refreshing alcoholic beverages, fruit liquor, and liqueur; luxury drinks such as green tea, tea, oolong tea, coffee, refreshing beverages and lactic acid beverages; seasonings such as soy sauce, sauce, vinegar, and sweet rice wine; canned, binned or pouched foods such as rice topped cooked beef and vegetable, rice boiled together with meat and vegetables in a small pot, steamed rice with red beans, curry roux and rice, and other precooked foods; semi-dry or concentrated foods such as liver pastes and other spreads, soups for buckwheat noodles or wheat noodles, and concentrated soups; dry foods such as instant noodles, instant curry roux, instant coffee, powder juice, powder soup, instant soybean paste (miso) soup, precooked foods, precooked beverages, and precooked soup; frozen foods such as sukiyaki, pot-steamed hotchpotch, split and grilled eel, hamburger steak, shao-mai, dumpling stuffed with minced pork, various sticks, and fruit cocktails; solid foods; liquid foods (soups); spices; and the like, in which each of the foods and beverages comprises the above-mentioned ingredient of the present invention.

In the food or beverage of the present invention, the above-mentioned compound usable as the effective ingredient in the present invention is, alone or in plurality, contained, added and/or diluted, and its shape is not particularly limited, as long as the compound is contained in an amount necessary for exhibiting its enhancing activity for NGF production. For instance, the shape includes those which can be taken orally such as tablets, granules and capsules.

The content of the above-mentioned effective ingredient in the food or beverage of the present invention is not particularly limited, and the content can be appropriately selected from the viewpoints of palatability and exhibition of activity. The content of the effective ingredient is, for instance, preferably 0.0001% by weight or more, more preferably from 0.0001 to 10% by weight, still more preferably from 0.0006 to 6% by weight of the food. Also, the content of the effective ingredient is, for instance, preferably 0.00001% by weight or more, more preferably from 0.0001 to 10% by weight, still more preferably from 0.0006 to 6% by weight, of the beverage. Also, it is desired that the food or beverage of the present invention may be taken such that the effective ingredient contained therein is taken, for instance, in an amount of preferably from 0.001 to 100 mg/kg weight, preferably from 0.1 to 10 mg/kg weight per day for adult.

In addition, the present invention provides a feed for an organism having an enhancing action for NGF production, wherein the above-mentioned effective ingredient is contained, added and/or diluted in the feed. In another embodiment, the present invention also provides a method of feeding an organism, characterized by administering the above-mentioned effective ingredient to the organism. In still another embodiment, the present invention provides an organism feeding agent characterized in that the organism feeding agent comprises the above-mentioned effective ingredient.

In these inventions, the organism includes, for instance, culturing or breeding animals, pet animals, and the like. The culturing or breeding animal is exemplified by cattle, experimental animals, poultry, pisces, crustaceae or shellfish. The feed is exemplified by a feed for sustenance of and/or improvement in physical conditions. The organism feeding agent includes immersion agents, feed additives, and beverage additives.

According to these inventions, the same effects can be expected to be exhibited as those of the above-mentioned therapeutic agent or prophylactic agent of the present invention, on the basis of the enhancing activity for NGF production of the above-mentioned effective ingredient usable in the present invention in the organism exemplified above for applying these. In other words, these inventions have a therapeutic or prophylactic effect for a disease requiring an enhancing action for NGF production in the organism.

The above-mentioned effective ingredient usable in the present invention is usually administered in an amount of preferably from 0.01 to 2000 mg per 1 kg of the subject organism per day, in which the effective ingredient is suitably administered in the form of the feed of the present invention. For instance, the effective ingredient can be added to and mixed with a raw material for an artificially formulated feed for applying to the subject animal, or the effective ingredient is mixed with a powder raw material for an artificially formulated feed, and thereafter the resulting mixture is further added to and mixed with other raw materials. The content of the above-mentioned effective ingredient in the feed is not particularly limited. The content can be appropriately set in accordance with its purposes, and an appropriate proportion in the feed is from 0.001 to 15% by weight.

The artificially formulated feed includes feeds using animal-derived raw materials such as fish meal, casein, and squid meal; plant-derived raw materials such as soybean grounds, flour, and starch; microorganism raw materials such as yeasts for feed; animal fats and oils such as cod-liver oil and squid-liver oil; vegetable fats and oils such as soybean oil and rapeseed oil; vitamins; minerals; amino acids; antioxidants; and the like as raw materials. In addition, feeds for fish such as fish minced meat are also included.

The method for preparing the feed of the present invention is not particularly limited. In addition, the formulation may be in accordance with those of general feeds, as long as the above-mentioned effective ingredient according to the present invention having enhancing action for NGF production is contained in the feed produced.

Also, the above-mentioned effective ingredient of the present invention having enhancing action for NGF production can be administered by directly adding the above-mentioned effective ingredient to water, seawater, or the like in a pool, a water tank, a water reservoir, or a feeding range, and immersing a subject organism into the resulting solution. The immersion method is especially effective when the amount of intake of the feed of the subject organism is lowered. The concentration of the effective ingredient according to the present invention having enhancing action for NGF production in water or seawater is not particularly limited, and the effective ingredient may be used in accordance with its purposes. It is appropriate that the concentration is preferably from 0.00001 to 1% by weight.

Also, a beverage comprising the above-mentioned effective ingredient according the present invention having enhancing action for NGF production may be given to a subject organism as a feeding drink. The concentration of the effective ingredient of the present invention having enhancing action for NGF production in the beverage is not particularly limited, and the effective ingredient may be used in accordance with its purposes. It is appropriate that the concentration is preferably from 0.0001 to 1% by weight. The organism feeding agent, for instance, an immersion agent, a feed additive, or a beverage additive comprising the above-mentioned effective ingredient of the present invention having enhancing action for NGF production may be prepared by known formulation and preparation method. The content of the effective ingredient in the organism feeding agent is not particularly limited, so long as the desired effects of the present invention can be obtained.

The organism to which the present invention can be applied is not limited. The culturing or breeding animals include cattle such as *Equus, Bos, Porcus, Ovis, Capra, Camelus,* and *Lama;* experimental animals such as mice, rats, guinea pigs, and rabbits; poultry such as *Chrysolophus*, ducks, *Meleagris*, and *Struthioniformes;* pisces such as *Pagrus, Oplegnathidae, Paralichthys,* plaice, *Seriola,* young *Seriola,* amberjack, *Thunna, Caranx delicatissimus, Plecoglossus, Salmo•Oncorhynchus, Fugu, Anguilla, Misguirus,* and *Parasilurus;* Crustaceae such as *Penaidae,* black tiger shrimp, *Penaeus roentalis,* and *Portulus trituberculatus;* and shellfish such as abalones (awabi), turban shells, scallops, and oysters; and the pet animals includes dogs, cats, and the like, so that the feed can be widely applied to animals on land and in water.

The method of feeding an organism of the present invention can be carried out by allowing an organism to take the effective ingredient of the present invention according to the method concretely illustrated as the method of its use.

By allowing a subject organism to take the feed comprising the above-mentioned effective ingredient usable in the present invention having enhancing action for NGF production, or immersing a subject organism into a solution containing the above-mentioned effective ingredient usable in the present invention having enhancing action for NGF production, the physical conditions of the cattle, experimental animals, poultry, pisces, Caustacea, shellfish, pet animals or the like can be well sustained and ameliorated.

As a still another embodiment of the present invention, there is provided use of the above-mentioned effective ingredient of the present invention in the preparation of a therapeutic agent or prophylactic agent for a disease requiring enhancement of NGF production, an enhancing agent for NGF production, or a food, beverage or feed for enhancing NGF production. The use embodiments include use embodiments of the above-mentioned effective ingredient in the preparation of the therapeutic agent or prophylactic agent, the enhancing agent for NGF production, or the food, beverage or feed for enhancing NGF production of the present invention mentioned above. For instance, as the use of the above-mentioned effective ingredient in the preparation of a therapeutic agent or prophylactic agent for a disease requiring enhancement of NGF production, or an enhancing agent for NGF production, there are exemplified the use in the preparation of a solid agent such as a tablet, a granule, a powder, a fine powder, and a capsule, a liquid agent such as a common liquid agent, a suspension agent, or an emulsion agent, or a dry product which can be liquefied by adding an appropriate carrier before use.

No toxicity is found when the above-mentioned effective ingredient usable in the present invention is administered in an amount effective for the exhibition of its action. For instance, in the case of oral administration, no cases of death are found when any one of 3'-O-β-D-glucopyranoyl khellactone, 7-O-β-D-glucopyranosyloxy-8-prenyl coumarin,
7-β-D-glucopyranosyloxy-6-prenyl coumarin,
4'-O-angeloyl-3 '-O-[6-O-(β-D-glucopyranosyl)-β-D-glucopyranosyl]-khellactone, 8-carboxyl-3-hydroxy-5-methoxy-2-dimethyl chroman,
3-hydroxy-8-[3-(4-hydroxyphenyl)-acryloyl]-5-methoxy-2-dimethyl chroman, an optically active isomer thereof or a salt thereof is orally administered to a rat in a single dose at 1 g/kg of the body weight. Also, incidence of adverse actions is not found.

EXAMPLES

The present invention will be more concretely described hereinbelow by means of the examples, without by no means limiting the scope of the present invention thereto. Unless specified otherwise, "%" in the examples means "% by weight."

Preparation Example 1

Fractionation of Fraction Derived from Root Portions of *Angelica keiskei* Koidz (1) Twenty-four liters of ethyl acetate was added to 5.8 kg of dry powder of root portions of *Angelica keiskei* koidz., and extraction was carried out at room temperature for 3 hours. Eighteen liters of ethanol was added to the residue after suction filtration, and extraction was carried out overnight at room temperature. Next, 52 liters of distilled water was added to the residue after suction filtration, and extraction was carried out at 60° C. for 3 hours. A liquid portion resulting from removal of the solid residue was concentrated with a rotary evaporator, and a 2.5-fold amount of ethanol was added to the concentrate, and the mixture was allowed to stand overnight at 4° C. Thereafter, the mixture was fractionated to precipitates and a liquid portion by suction filtration. The liquid portion was concentrated to dryness with a rotary evaporator, to give a water-extracted, low-molecular fraction of root portions of *Angelica keiskei* koidz. Thereafter, the water-extracted, low-molecular fraction of root portions of *Angelica keiskei* koidz. was applied to Amberlite XAD-2 (manufactured by Organo; amount of resin: 2 liters), and non-adsorbed substances were sufficiently washed out with 30 liters of distilled water. Next, the adsorbed substances were eluted with 16 liters of methanol. The methanol eluate was concentrated to dryness with a rotary evaporator, to give a water-extracted, low-molecular XAD-2-treated fraction of root portions of *Angelica keiskei* koidz.

(2) The water-extracted, low-molecular XAD-2-treated fraction of root portions of *Angelica keiskei* koidz. described in item (1) of Preparation Example 1 was fractionated using reverse phase chromatography. The conditions therefor are given below. The resin used was Cosmosil 140 $C_{18}$-OPN (manufactured by Nakalai Tesque Inc., amount of resin: 400 ml). The water-extracted, low-molecular XAD-2-treated fraction of root portions of *Angelica keiskei* koidz. was applied to the column packed with the above resin, and elution was carried out using subsequently 1 liter each of distilled water, a 20% aqueous acetonitrile solution, a 25% aqueous acetonitrile solution, a 40% aqueous acetonitrile solution, and methanol as the developing solvents. Each eluted fraction was concentrated under reduced pressure, to prepare each product fractionated by Cosmosil.

(3) The fraction eluted with a 25% aqueous acetonitrile solution from Cosmosil 140 obtained in item (2) of Preparation Example 1 was fractionated using reverse phase chromatography. The conditions therefor are given below. The column used was TSK gel ODS 80Ts (21.5 mm×30 cm, manufactured by Tosoh Corporation). The elution ratio of Solvent A (distilled water) and Solvent B (mixture of distilled water and acetonitrile in a volume ratio of 1:1) was such that the ratio of Solvent B was increased linearly from 25 to 100% from 0 to 120 minutes, the ratio of Solvent B was retained at 100% for the subsequent 20 minutes, and the ratio of Solvent B was finally decreased to 25% and retained thereat for 20 minutes. The elution rate was 5 ml/minute, and the detection was carried out at 215 nm. The fractions 1 to 30 were collected using ultraviolet absorption as an index.

Example 1

Enhancing Activity for NGF Production of 3'-O-β-D-glucopyranoyl khellactone (1) The mass spectrum (MS) of the fraction 10 derived from root portions of *Angelica keiskei* koidz. (fraction including a peak detected at a retention time of 62.2 minutes) obtained in item (3) of Preparation Example 1 was measured with a mass spectrometer (DX302, manufactured by JEOL LTD.) by FAB-MS technique. As the matrix, glycerol was used. As a result, a peak of m/z 245 (M-OGlc)$^+$ was detected. FIG. 1 shows the FAB-MS spectrum of the fraction 10 derived from root portions of *Angelica keiskei* koidz. In FIG. 1, the axis of abscissas is m/z value, and the axis of ordinates is relative intensity.

The structure of the fraction 10 derived from root portions of *Angelica keiskei* koidz. was analyzed by measuring various NMR spectra using nuclear magnetic resonance (NMR) spectrometer (JNM-A500, manufactured by JEOL, Ltd.). The signals of NMR are shown below.

$^1$H-NMR: δ 1.36 (3H, s, 2'-CH$_3$), 1.37 (3H, s, 2'-CH$_3$), 3.08 (2H, m, 2"-H and 4"-H), 3.12 (1H, m, 3"-H), 3.41 (1H, m, 5"-H), 3.81 (1H, d, J=4.5 Hz, 3'-H), 4.11 (1H, dd, J=7.0, 11.5 Hz, 6"-H), 4.35 (1H, brd, J=11.5 Hz, 6"-H), 4.53 (1H, d, J=7.5 Hz, 1"-H), 5.14 (1H, d, J=4.5 Hz, 4'-H), 6.28 (1H, d, J=9.5 Hz, 3-H), 6.78 (1H, d, J=8.5 Hz, 6-H), 7.54 (1H, d, J=8.5 Hz, 5-H), 7.98 (1H, d, J=9.5 Hz, 4-H)

Figure 2:
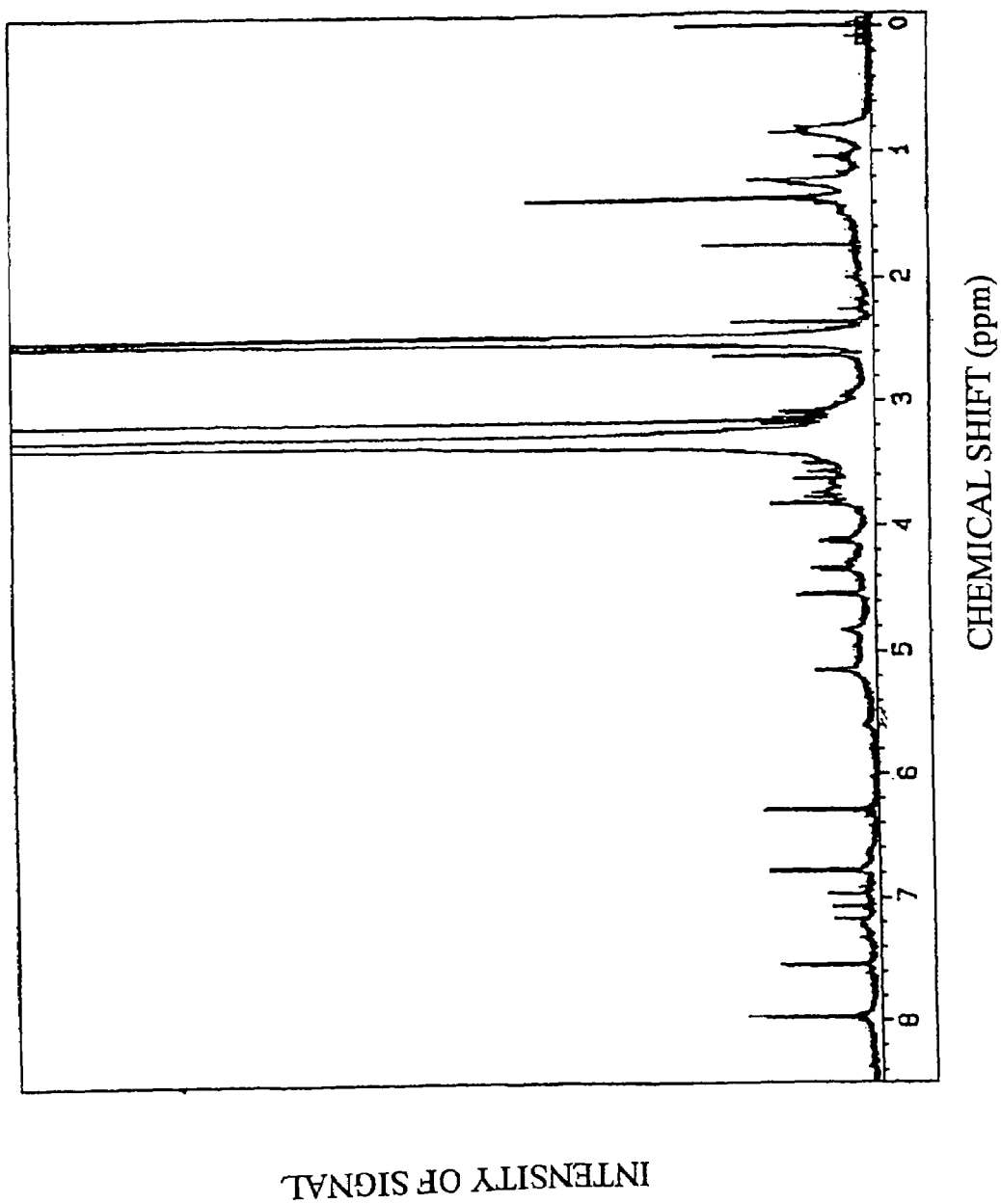
FIG. 2 is a chart showing $^1$H-NMR spectrum of the fraction 10 from root portions of Angelica keiskei koidz.

Here, in $^1$H-NMR, the sample was dissolved in deuterated dimethyl sulfoxide, and the chemical shift of the residual dimethyl sulfoxide was expressed as 2.49 ppm. FIG. 2 shows $^1$H-NMR spectrum of the fraction 10 derived from root portions of *Angelica keiskei* koidz. In FIG. 2, the axis of abscissas is chemical shift (ppm), and the axis of ordinates is intensity of signal.

As a result of the analyses of the MS spectrum and NMR spectra for the fraction 10 derived from root portions of *Angelica keiskei* koidz., it was identified that the component is 3'-O-β-D-glucopyranoyl khellactone (molecular weight: 424).

(2) The enhancing activity for NGF production was determined for the fraction 10 derived from root portions of *Angelica keiskei* koidz., of which structure was identified in item (1) of Example 1. L-M cells (ATCC CCL-1.2) from murine fibroblasts were suspended in an M199 medium (manufactured by ICN) containing 0.5% bactopeptone (manufactured by Gibco) so as to have a concentration of 1.5×10$^5$ cells/ml. The suspension was put in a 96 well plate in an amount of 0.1 ml each well, and the cells were aseptically cultured. After culturing the cells for 3 days, the medium was removed therefrom, and exchanged with an M199 medium containing 0.5% bovine serum albumin (manufactured by Sigma). The fraction 10 derived from root portions of *Angelica keiskei* koidz. was added as the sample thereto, and the cells were cultured for 20 hours. After the termination of the culture, the concentration of the NGF in the culture medium was assayed by an enzyme immunoassay method (NGF Emax Immuno Assay System, manufactured by Promega). The NGF concentration when added was expressed, assuming that the NGF concentration in the cell culture medium with no addition of the sample is 100%, whereby the enhancing activity for NGF production of the sample was evaluated. The sample was added so as to have a final concentration shown in Table 1. The experiment was carried out twice, and an average value was taken. As a result, it was clarified that the fraction 10 derived from root portions of *Angelica keiskei* koidz., namely 3'-O-β-D-glucopyranoyl khellactone, has an enhancing activity for NGF production. The results are shown in Table 1.

TABLE 1

| Fractionated Fraction (Detected Peaks: minutes) | Concentration (mg/ml) | Amount of NGF Produced (%) |
|---|---|---|
| Fraction 10 (62.2) | 2.00 | 565.5 |

(Here, the amount of NGF produced in the control was 0.382 ng/ml.)

Example 2

Enhancing Activity for NGF Production of 7-O-β-D-Glucopyranosyloxy-8-prenyl coumarin (1) The fraction 13 (the fraction including the peak detected at a retention time of 66.9 minutes) obtained in item (3) of Preparation Example 1 was further fractionated using reverse phase chromatography. The conditions therefor are given below. The column used was TSK gel ODS 80TsQA (4.6 mm×25 cm, manufactured by Tosoh Corporation). The elution ratio of Solvent A (distilled water containing 0.1% trifluoroacetic acid) and Solvent B (mixture of distilled water and acetonitrile in a volume ratio of 1:1, containing 0.1% trifluoroacetic acid) was such that the ratio of Solvent B was retained at 50% for 20 minutes. The elution rate was 1 ml/minute, and the detection was carried out at 235 nm. The fractions 13-1 to 13-8 were collected using ultraviolet absorption as an index.

(2) The MS spectrum and the NMR spectra of the fraction 13-2 derived from root portions of *Angelica keiskei* koidz. (the fraction including the peak at the retention time of 8.7 minutes) obtained in item (1) of Example 2 were determined in the same manner as in item (1) of Example 1.

Figure 3:
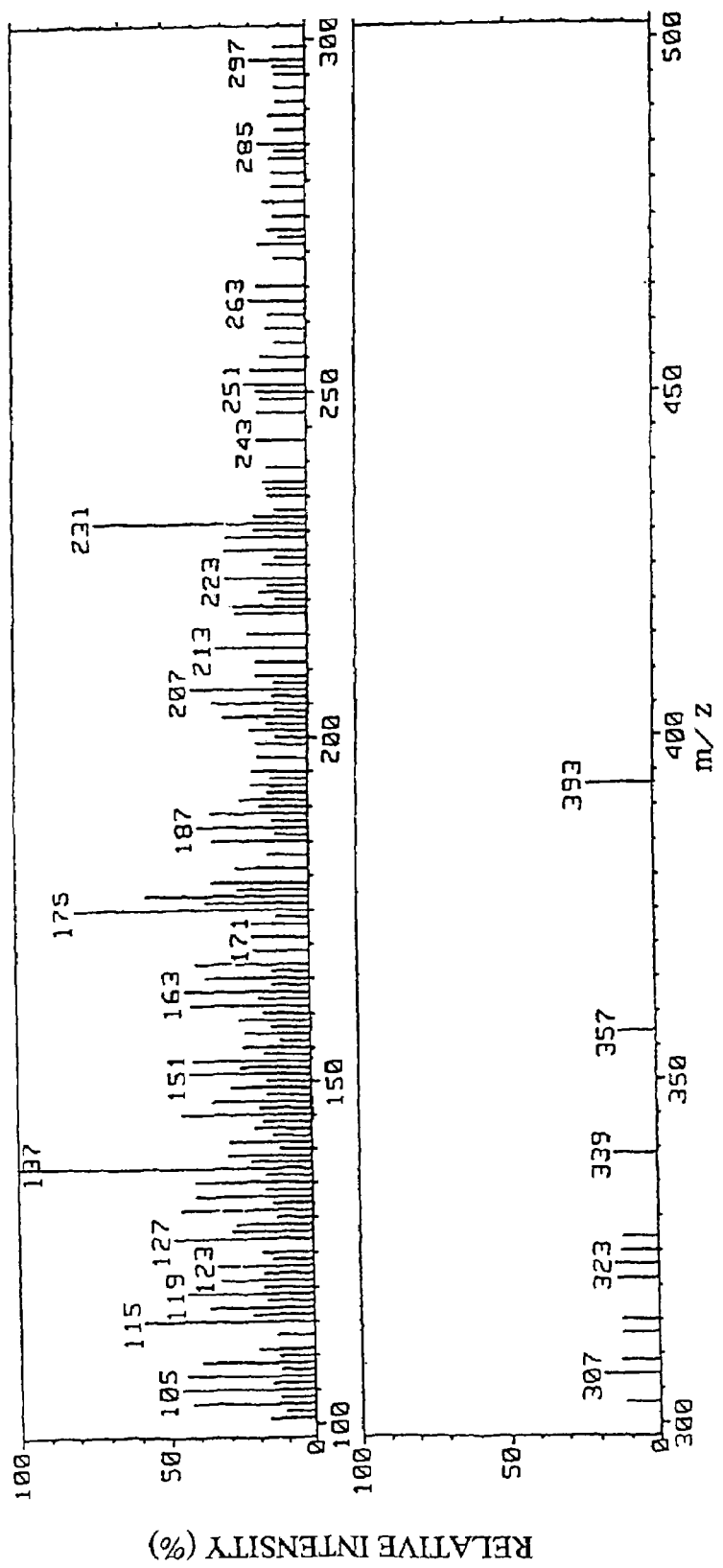
FIG. 3 is a chart showing FAB-MS spectrum of the fraction 13-2 from root portions of Angelica keiskei koidz.

According to the mass spectroscopy, a peak of m/z 393 (M+H)$^+$ was detected. FIG. 3 shows the MS spectrum of the fraction 13-2 derived from root portions of *Angelica keiskei* koidz. In FIG. 3, the axis of abscissas is m/z value, and the axis of ordinates is relative intensity.

The signals of NMR for the fraction 13-2 derived from root portions of *Angelica keiskei* koidz. are shown below.

$^1$H-NMR: δ 1.61 (3H, s, 3'-CH$_3$), 1.78 (3H, s, 3'-CH$_3$), 3.17 (1H, t, J=9.5 Hz, 4"-H), 3.28 (1H, m, 3"-H), 3.29 (1H, m, 2"-H), 3.38 (1H, m, 5"-H), 3.40 (1H, m, 1'-H), 3.46 (1H, m, 6"-H), 3.58 (1H, m, 1'-H), 3.69 (1H, m, 6"-H), 4.94 (1H, d, J=7.5 Hz, 1"-H), 5.20 (1H, m, 2'-H), 6.30 (1H, d, J=9.5 Hz, 3-H), 7.11 (1H, d, J=8.5 Hz, 6-H), 7.51 (1H, d, J=8.5 Hz, 5-H), 7.98 (1H, d, J=9.5 Hz, 4-H)

Figure 4:
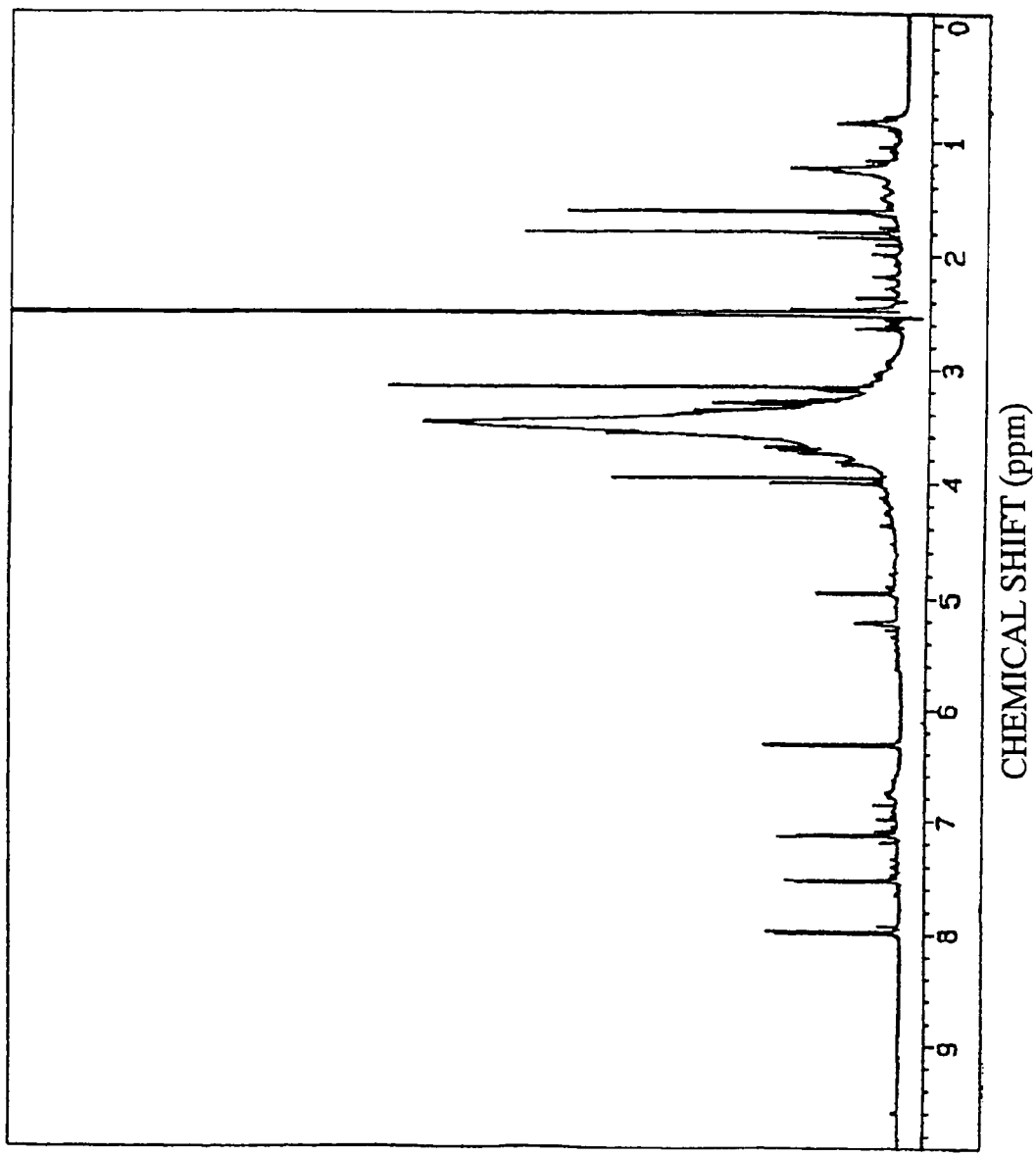
FIG. 4 is a chart showing $^1$H-NMR spectrum of the fraction 13-2 from root portions of Angelica keiskei koidz.

FIG. 4 shows $^1$H-NMR spectrum of the fraction 13-2 derived from root portions of *Angelica keiskei* koidz. In FIG. 4, the axis of abscissas is chemical shift (ppm), and the axis of ordinates is intensity of signal.

$^{13}$C-NMR: δ 17.8 (3'-CH$_3$), 21.6 (1'-c), 25.5 (3'-CH$_3$), 60.6 (6"-c), 69.7 (4"-c), 73.4 (2"-c), 76.7 (3"-c), 77.1 (5"-c), 100.8 (1"-c), 111.5 (6-c), 112.8 (3-c), 113.4 (10-c), 117.4 (8-c), 121.3 (2'-c), 126.8 (5-c), 131.5 (3'-c), 144.5 (4-c), 152.1 (9-c), 157.8 (7-c), 160.2 (2-c)

Figure 5:
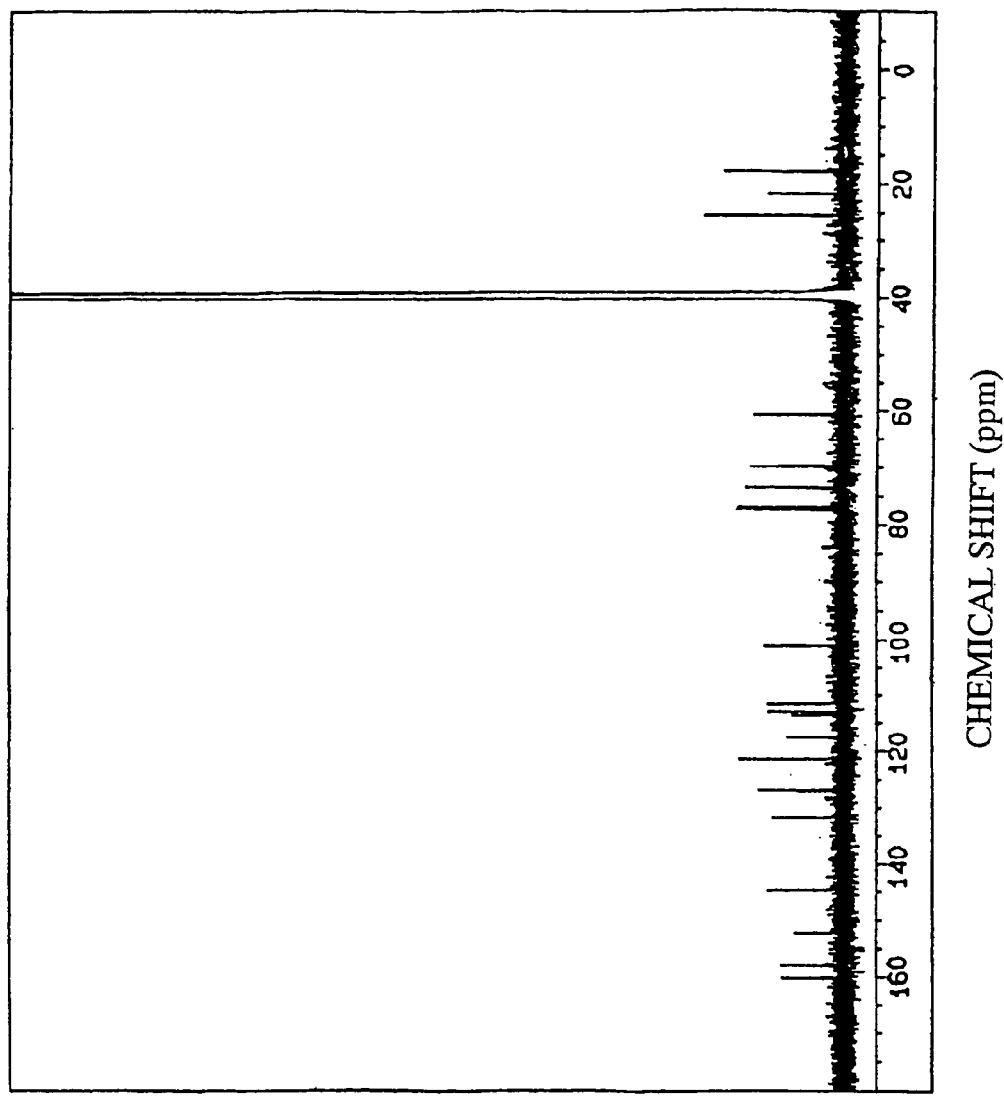
FIG. 5 is a chart showing $^{13}$C-NMR spectrum of the fraction 13-2 from root portions of Angelica keiskei koidz.

Here, in $^{13}$C-NMR, the sample was dissolved in deuterated dimethyl sulfoxide, and the chemical shift of the deuterated dimethyl sulfoxide was expressed as 39.5 ppm. FIG. 5 shows $^{13}$C-NMR spectrum of the fraction 13-2 derived from root portions of *Angelica keiskei* koidz. In FIG. 5, the axis of abscissas is chemical shift (ppm), and the axis of ordinates is intensity of signal.

As a result of the analyses of the MS spectrum and NMR spectra for the fraction 13-2 derived from root portions of *Angelica keiskei* koidz., it was identified that the component is 7-O-β-D-glucopyranosyloxy-8-prenyl coumarin (molecular weight: 392).

(3) The enhancing activity for NGF production of the fraction 13-2 derived from root portions of *Angelica keiskei* koidz. used as a sample, of which structure was identified in item (2) of Example 2, was determined in the same manner as in item (2) of Example 1. The sample was added so as to have the final concentration as shown in Table 2. As a result, it was clarified that the fraction 13-2 derived from root portions of *Angelica keiskei* koidz., namely 7-O-β-D-glucopyranosyloxy-8-prenyl coumarin, has an enhancing activity for NGF production. The results are shown in Table 2.

TABLE 2

| Fractionated Fraction (Detected Peaks: minutes) | Concentration (mg/ml) | Amount of NGF Produced (%) |
| --- | --- | --- |
| Fraction 13-2 (8.7) | 1.00 | 792.1 |

(Here, the amount of NGF produced in the control was 0.053 ng/ml.)

Example 3

Enhancing Activity for NGF Production of 8-Carboxyl-3-hydroxy-5-methoxy-2-dimethyl chroman (1) The fraction 18 (the fraction including the peaks detected at retention time of 73.0, 73.8 and 74.97 minutes) obtained in item (3) of Preparation Example 1 was further fractionated to fractions 18-1 to 18-12 using reverse phase chromatography in the same manner as in item (1) of Example 2.

(2) The MS spectrum and the NMR spectra of the fraction 18-4 derived from root portions of *Angelica keiskei* koidz. (the fraction including the peak detected at a retention time of 10.9 minutes) obtained in item (1) of Example 3 were determined in the same manner as in item (2) of Example 2.

Figure 6:
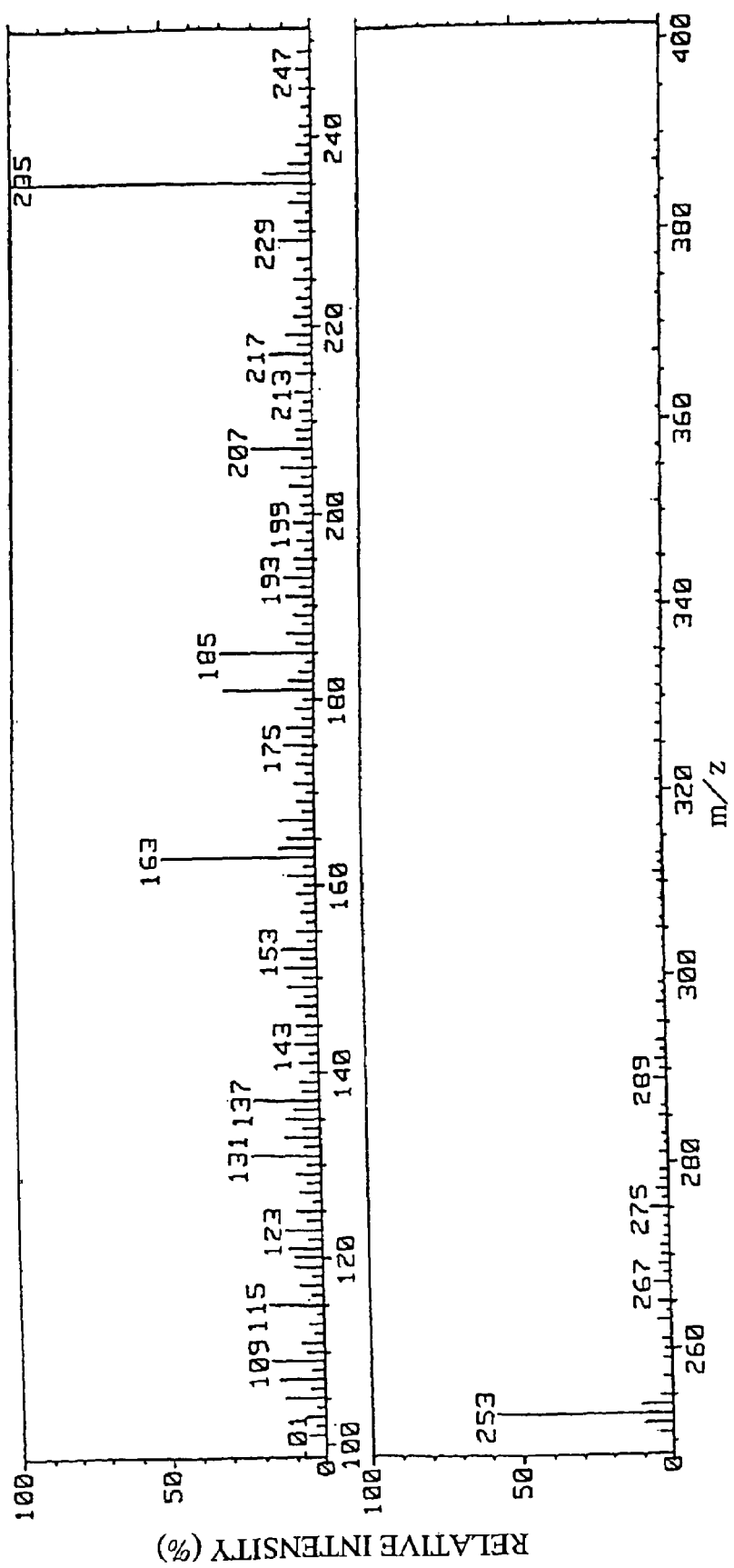
FIG. 6 is a chart showing FAB-MS spectrum of the fraction 18-4 from root portions of Angelica keiskei koidz.

According to the mass spectroscopy, a peak of m/z 253 $(M+H)^+$ was detected. FIG. 6 shows the MS spectrum of the fraction 18-4 derived from root portions of *Angelica keiskei* koidz. In FIG. 6, the axis of abscissas is m/z value, and the axis of ordinates is relative intensity.

The signals of NMR are shown below.

$^1$H-NMR: δ 1.15 (3H, s, 2-CH$_3$), 1.27 (3H, s, 2-CH$_3$), 2.39 (1H, dd, J=8.0, 17.0 Hz, 4-H), 2.76 (1H, dd, J=5.0, 17.0 Hz, 4-H), 3.62 (1H, m, 3-H), 3.81 (3H, s, 5-OCH$_3$), 5.16 (1H, d, J=4.5 Hz, 3-OH), 6.56 (1H, d, J=9.0 Hz, 6-H), 7.59 (1H, d, J=9.0 Hz, 10-H), 11.86 (1H, brs, 8-COOH)

Figure 7:
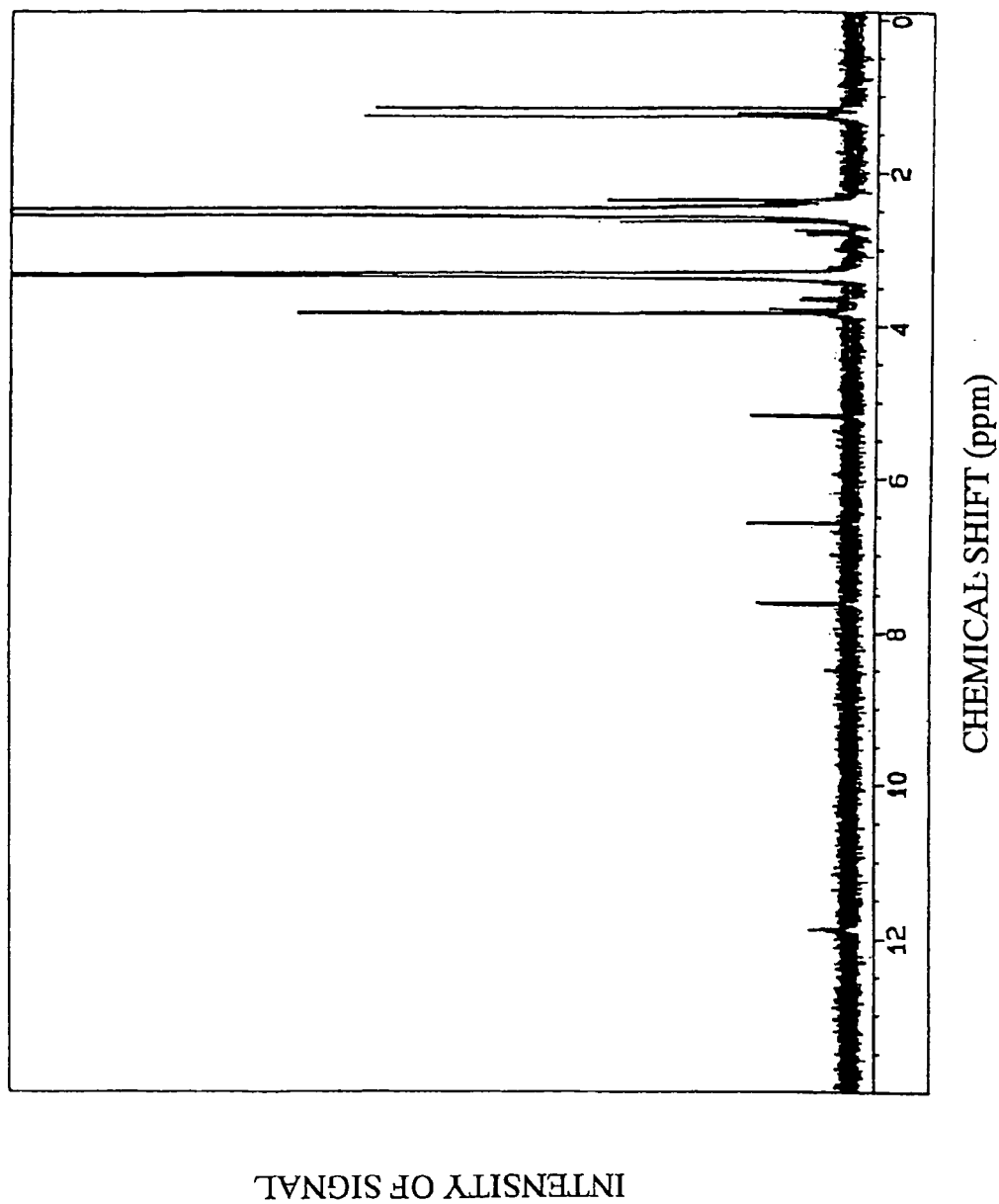
FIG. 7 is a chart showing $^1$H-NMR spectrum of the fraction 18-4 from root portions of Angelica keiskei koidz.

FIG. 7 shows $^1$H-NMR spectrum of the fraction 18-4 derived from root portions of *Angelica keiskei* koidz. In FIG. 7, the axis of abscissas is chemical shift (ppm), and the axis of ordinates is intensity of signal.

$^{13}$C-NMR: δ 20.4 (2-CH$_3$), 25.4 (2-CH$_3$), 26.2 (4-C), 55.7 (5-OCH$_3$), 67.0 (3-C), 77.6 (2-C), 101.8 (6-C), 109.4 (10-C), 112.5 (8-C), 130.7 (7-C), 153.3 (9-C), 160.4 (5-C), 166.6 (8-COOH)

Figure 8:
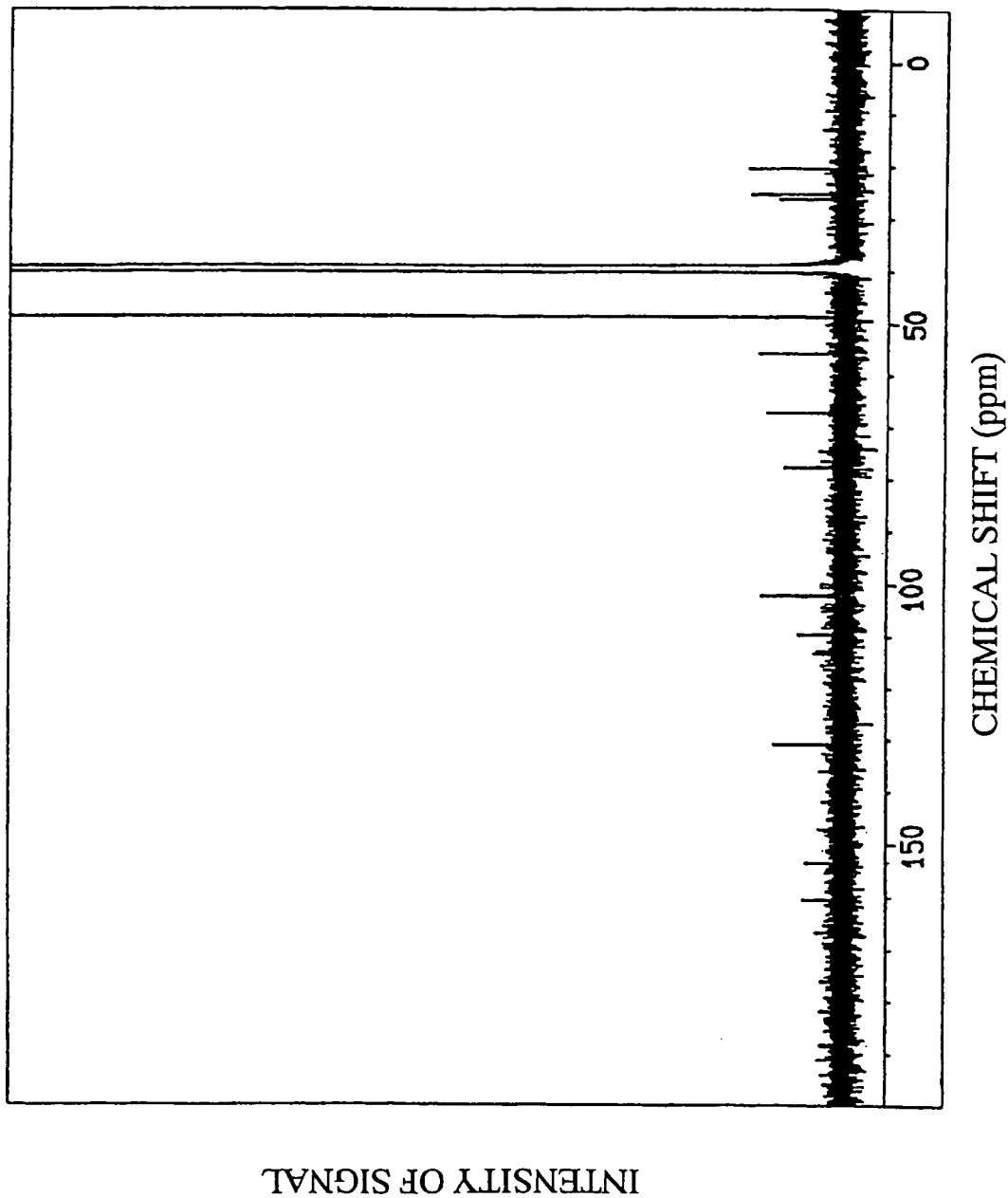
FIG. 8 is a chart showing $^{13}$C-NMR spectrum of the fraction 18-4 from root portions of Angelica keiskei koidz.

FIG. 8 shows $^{13}$C-NMR spectrum of the fraction 18-4 derived from root portions of *Angelica keiskei* koidz. In FIG. 8, the axis of abscissas is chemical shift (ppm), and the axis of ordinates is intensity of signal.

As a result of the analyses of the MS spectrum and NMR spectra for the fraction 18-4 derived from root portions of *Angelica keiskei* koidz., it was identified that the component is 8-carboxyl-3-hydroxy-5-methoxy-2-dimethyl chroman (molecular weight: 252).

(3) The enhancing activity for NGF production of the fraction 18-4 derived from root portions of *Angelica keiskei* koidz. used as a sample, of which structure was identified in item (2) of Example 3, was determined in the same manner as in item (2) of Example 1. The sample was added so as to have the final concentration as shown in Table 3. As a result, it was clarified that the fraction 18-4 derived from root portions of *Angelica keiskei* koidz., namely 8-carboxyl-3-hydroxy-5-methoxy-2-dimethyl chroman, has an enhancing activity for NGF production. The results are shown in Table 3.

TABLE 3

| Fractionated Fraction (Detected Peaks: minutes) | Concentration (mg/ml) | Amount of NGF Produced (%) |
| --- | --- | --- |
| Fraction 18-4 (10.9) | 0.0375 | 2510.4 |

(Here, the amount of NGF produced in the control was 0.027 ng/ml.)

Example 4

Enhancing Activity for NGF Production of 7-β-D-Glucopyranosyloxy-6-prenyl coumarin (1) The fraction 19 (the fraction including a peak detected at retention time of 75.4 minutes) and the fraction 20 (the fraction including a peak detected at 76.5 minutes), obtained in item (3) of Preparation Example 1, were mixed, and the mixture was further fractionated to fractions 19/20-1 to 19/20-7 using reverse phase chromatography in the same manner as in item (1) of Example 2.

(2) The MS spectrum and the NMR spectra of the fraction 19/20-5 (the fraction including the detection peak at the retention time of 16.4 minutes) derived from root portions of *Angelica keiskei* koidz. obtained in item (1) of Example 4 were determined in the same manner as in item (2) of Example 2.

Figure 9:
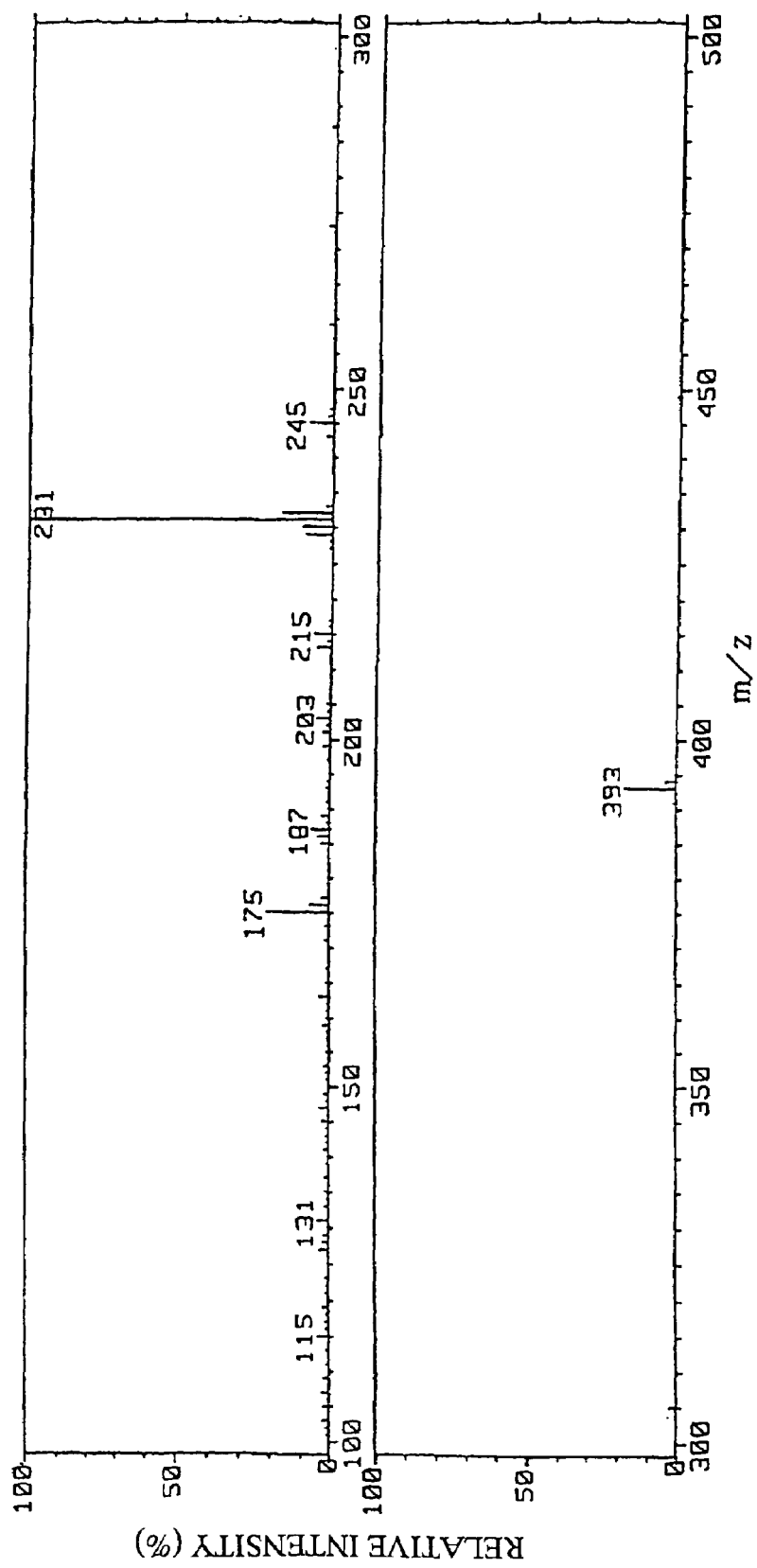
FIG. 9 is a chart showing FAB-MS spectrum of the fraction 19/20-5 from root portions of Angelica keiskei koidz.

According to the mass spectroscopy, a peak of m/z 393 $(M+H)^+$ was detected. FIG. 9 shows the MS spectrum of the fraction 19/20-5 derived from root portions of *Angelica keiskei* koidz. In FIG. 9, the axis of abscissas is m/z value, and the axis of ordinates is relative intensity.

The signals of NMR are shown below.

$^1$H-NMR: δ 1.67 (3H, s, 3'-CH$_3$), 1.69 (3H, s, 3'-CH$_3$), 3.15 (1H, m, 4"-H), 3.29 (3H, m, 1'-H, 2"-H and 3"-H), 3.37 (1H, dd, J=7.5, 15.5 Hz, 1'-H), 3.45 (2H, m, 5"-H and 6"-H), 3.72 (1H, dd, J=10.5, 6"-H), 4.97 (1H, d, J=7.5 Hz, 1"-H), 5.31 (1H, t, J=7.5 Hz, 2'-H), 6.28 (1H, d, J=9.0 Hz, 3-H), 7.07 (1H, s, 5-H), 7.41 (1H, s, 8-H), 7.98 (1H, d, J=9.0 Hz, 4-H)

Figure 10:
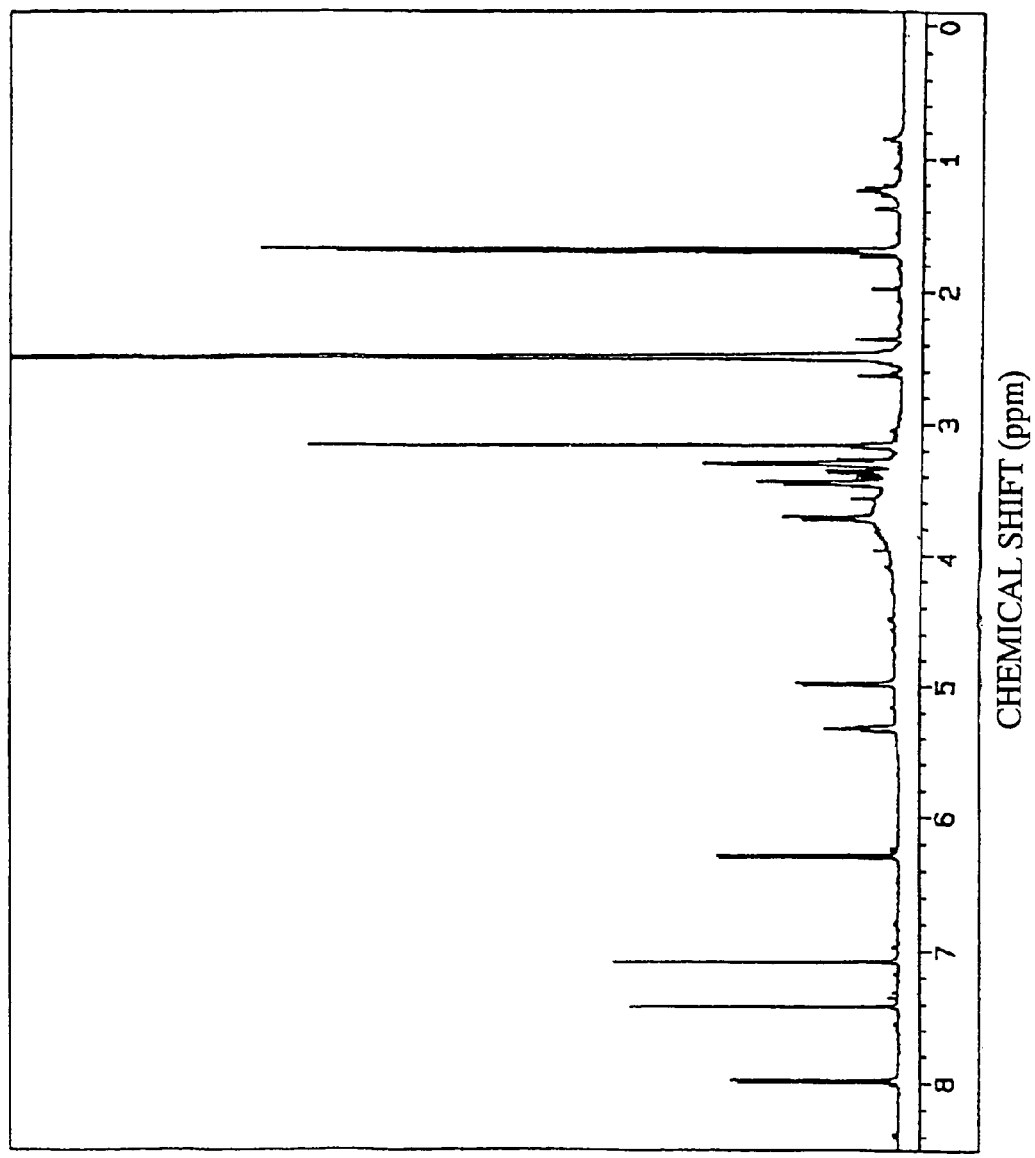
FIG. 10 is a chart showing $^1$H-NMR spectrum of the fraction 19/20-5 from root portions of Angelica keiskei koidz.

FIG. 10 shows $^1$H-NMR spectrum of the fraction 19/20-5 derived from root portions of *Angelica keiskei* koidz. In FIG. 10, the axis of abscissas is chemical shift (ppm), and the axis of ordinates is intensity of signal.

$^{13}$C-NMR: δ 17.6 (3'-CH$_3$), 25.5 (3'-CH$_3$), 27.4 (1'-C), 60.6 (6"-C), 69.6 (4"-C), 73.1 (2"-C), 76.3 (3"-C), 77.0 (5"-C), 100.4 (1"-C), 102.0 (8-C), 112.8 (10-C), 112.9 (3-C), 121.8 (2'-C), 127.4 (6-C), 128.0 (5-C), 132.4 (3'-C), 144.4 (4-C), 153.4 (9-C), 157.9 (7-C), 160.6 (2-C)

Figure 11:
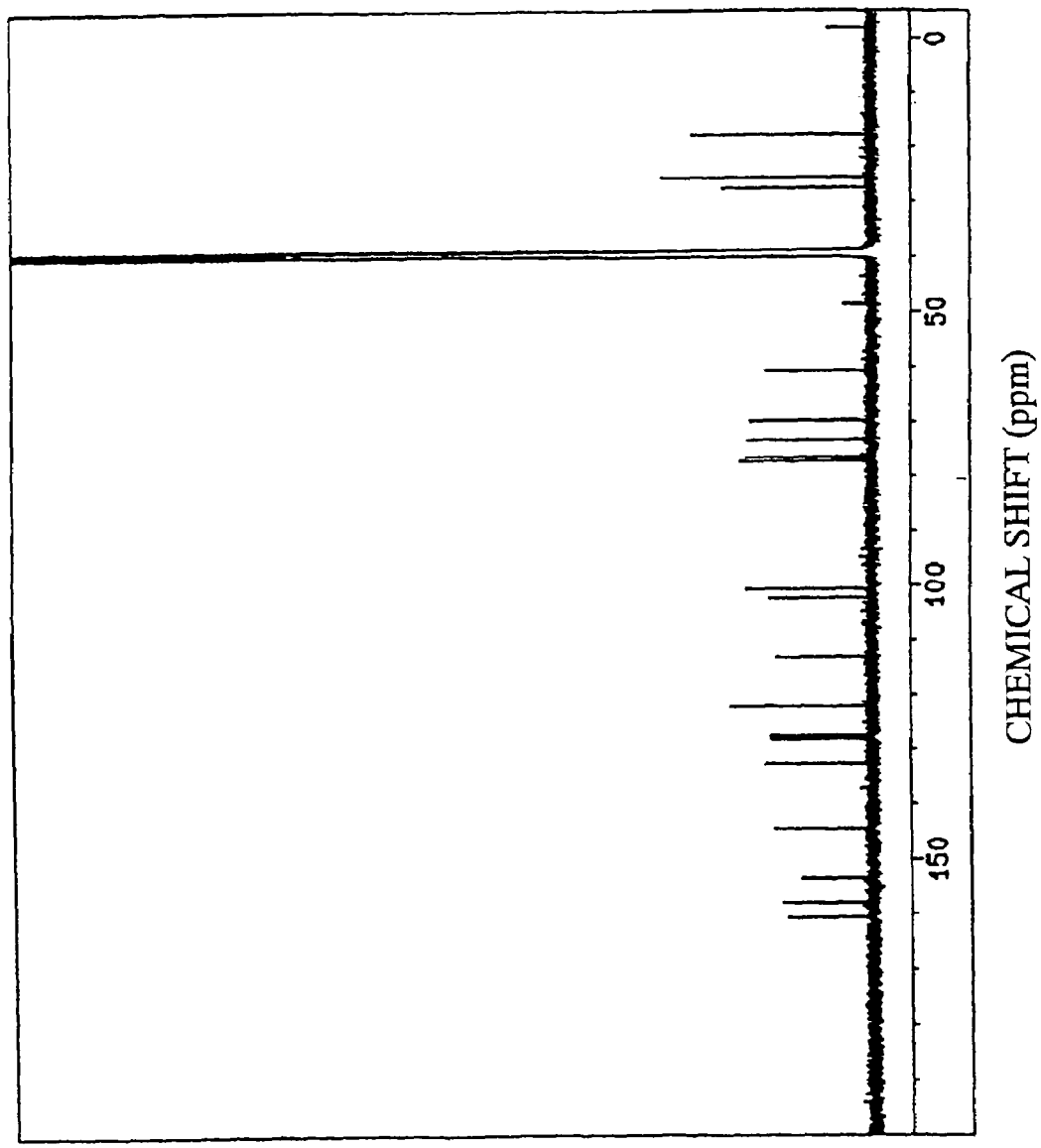
FIG. 11 is a chart showing $^{13}$C-NMR spectrum of the fraction 19/20-5 from root portions of Angelica keiskei koidz.

FIG. 11 shows $^{13}$C-NMR spectrum of the fraction 19/20-5 derived from root portions of *Angelica keiskei* koidz. In FIG.

11, the axis of abscissas is chemical shift (ppm), and the axis of ordinates is intensity of signal.

As a result of the analyses of the MS spectrum and NMR spectra for the fraction 19/20-5 derived from root portions of *Angelica keiskei* koidz., it was identified that the component is 7-β-D-glucopyranosyloxy-6-prenyl coumarin (molecular weight: 392).

(3) The enhancing activity for NGF production of the fraction 19/20-5 derived from root portions of *Angelica keiskei* koidz. used as a sample, of which structure was identified in item (2) of Example 4, was determined in the same manner as in item (2) of Example 1. The sample was added so as to have the final concentration as shown in Table 4. As a result, it was clarified that the fraction 19/20-5 derived from root portions of *Angelica keiskei* koidz., namely 7-β-D-glucopyranosyloxy-6-prenyl coumarin, has an enhancing activity for NGF production. The results are shown in Table 4.

TABLE 4

| Fractionated Fraction (Detected Peaks: minutes) | Concentration (mg/ml) | Amount of NGF Produced (%) |
|---|---|---|
| Fraction 19/20-5 (16.4) | 1.00 | 487.9 |

(Here, the amount of NGF produced in the control was 0.063 ng/ml.)

Example 5

Enhancing Activity for NGF Production of 4'-O-Angeloyl-3'-O-[6-O-(β-D-glucopyranosyl)-β-D-glucopyranosyl]-khellactone (1) The MS spectrum and the NMR spectra of the fraction 19/20-6 (the fraction including the detection peak at the retention time of 18.8 minutes) derived from root portions of *Angelica keiskei* koidz. obtained in item (1) of Example 4 were determined in the same manner as in item (2) of Example 2.

Figure 12:
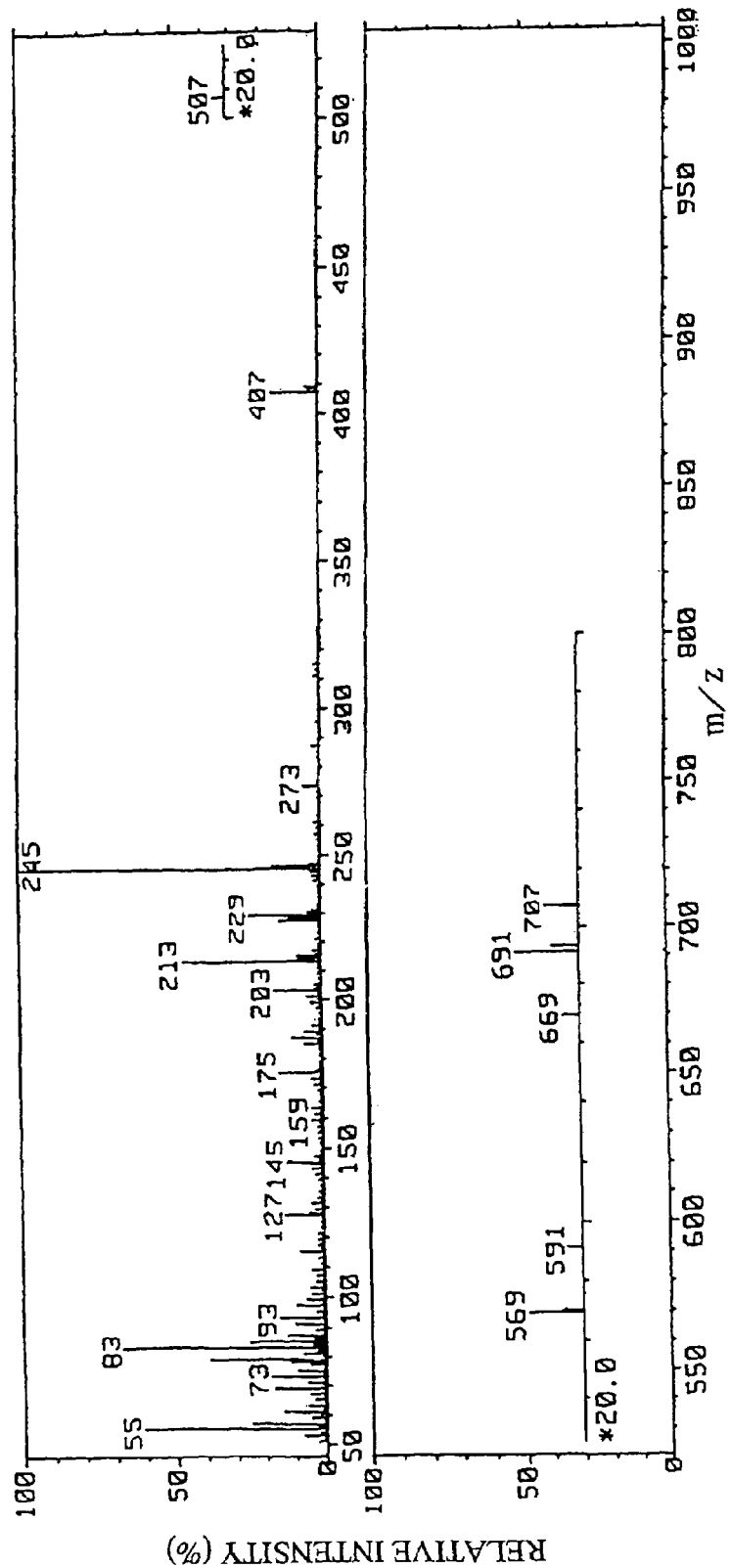
FIG. 12 is a chart showing FAB-MS spectrum of the fraction 19/20-6 from root portions of Angelica keiskei koidz.

Using a mass spectrometer, peaks of m/z 245 (M-2Glc-Angel)$^+$, 669 (M+H)$^+$, 691 (M+Na)$^+$ and 707 (M+K)$^+$ were detected. FIG. 12 shows the MS spectrum of the fraction 19/20-6 derived from root portions of *Angelica keiskei* koidz. In FIG. 12, the axis of abscissas is m/z value, and the axis of ordinates is relative intensity.

The signals of NMR are shown below.

$^1$H-NMR: δ 1.36(3H, s, 2'-CH$_3$), 1.43 (3H, s, 2'-CH$_3$), 1.79 (3H, brs, 2"-CH$_3$), 1.86 (3H, brd, J=7.0 Hz, 3"-CH$_3$), 2.90 (1H, t, J=8.0 Hz, 2b-H), 2.99 (1H, m, 2a-H), 3.01 (1H, m, 4a-H), 3.02 (1H, m, 4b-H), 3.05 (1H, m, 3b-H), 3.13 (1H, t, J=9.5 Hz, 3a-H), 3.35 (1H, m, 5a-H), 3.39 (1H, m, 5b-H), 3.39 (1H, m, 6b-H), 3.49 (1H, dd, J=8.0, 11.0 Hz, 6a-H), 3.64 (1H, d, J=11.5 Hz, 6b-H), 4.02 (1H, d, J=11.0 Hz, 6a-H), 4.21 (1H, d, J=8.0 Hz, 1b-H), 4.37 (1H, d, J=4.5 Hz, 3'-H), 4.46 (1H, brs, 6b-OH), 4.48 (1H, d, J=7.5 Hz, 1a-H), 4.51 (1H, brs, 2a-OH), 4.72 (1H, brs, 3b-OH), 4.83 (1H, brs, 2b-OH), 4.86 (1H, brs, 4a-OH), 5.03 (2H, brs, 4b-OH, 3a-OH), 5.96 (1H, brq, J=7.0 Hz, 3"-H), 6.26 (1H, d, J=9.5 Hz, 3-H), 6.61 (1H, d, J=4.5 Hz, 4'-H), 6.83 (1H, d, J=8.5 Hz, 6-H), 7.59 (1H, d, J=8.5 Hz, 5-H), 7.96 (1H, d, J=9.5 Hz, 4-H)

Figure 13:
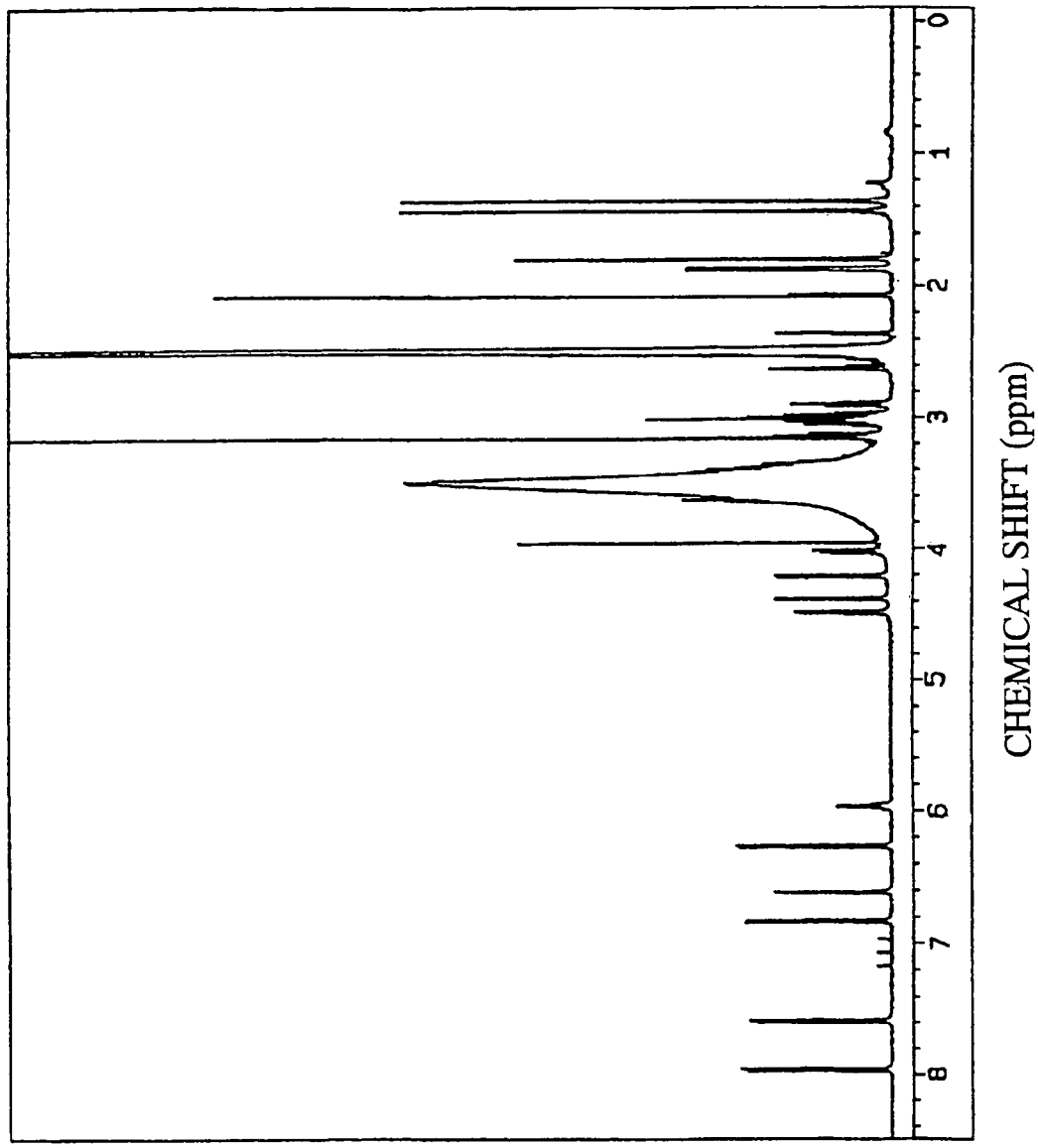
FIG. 13 is a chart showing $^1$H-NMR spectrum of the fraction 19/20-6 from root portions of Angelica keiskei koidz.

FIG. 13 shows $^1$H-NMR spectrum of the fraction 19/20-6 derived from root portions of *Angelica keiskei* koidz. In FIG. 13, the axis of abscissas is chemical shift (ppm), and the axis of ordinates is intensity of signal.

$^{13}$C-NMR: δ 15.2 (3"-CH$_3$), 20.0 (2"-CH$_3$), 21.3 (2'-CH$_3$), 26.4 (2-CH$_3$), 59.1 (4'-C), 61.0 (6b-C), 69.2 (6a-C), 70.0 (glucose-C), 70.4 (glucose-C), 73.4 (glucose-C), 73.7 (3'-C), 73.9 (glucose-C), 76.1 (glucose-C), 76.55 (glucose-C), 76.59 (glucose-C), 76.8 (glucose-C), 77.8 (2'-C), 100.5 (1a-C), 103.8 (1b-C), 107.7 (8-C), 112.1 (3-C), 112.1 (10-C), 114.2 (6-C), 128.0 (2"-C), 129.8 (5-C), 136.1 (3"-C), 144.5 (4-C), 153.6 (9-C), 156.2 (7-C), 159.4 (2-C), 166.3 (1"-C)

Figure 14:
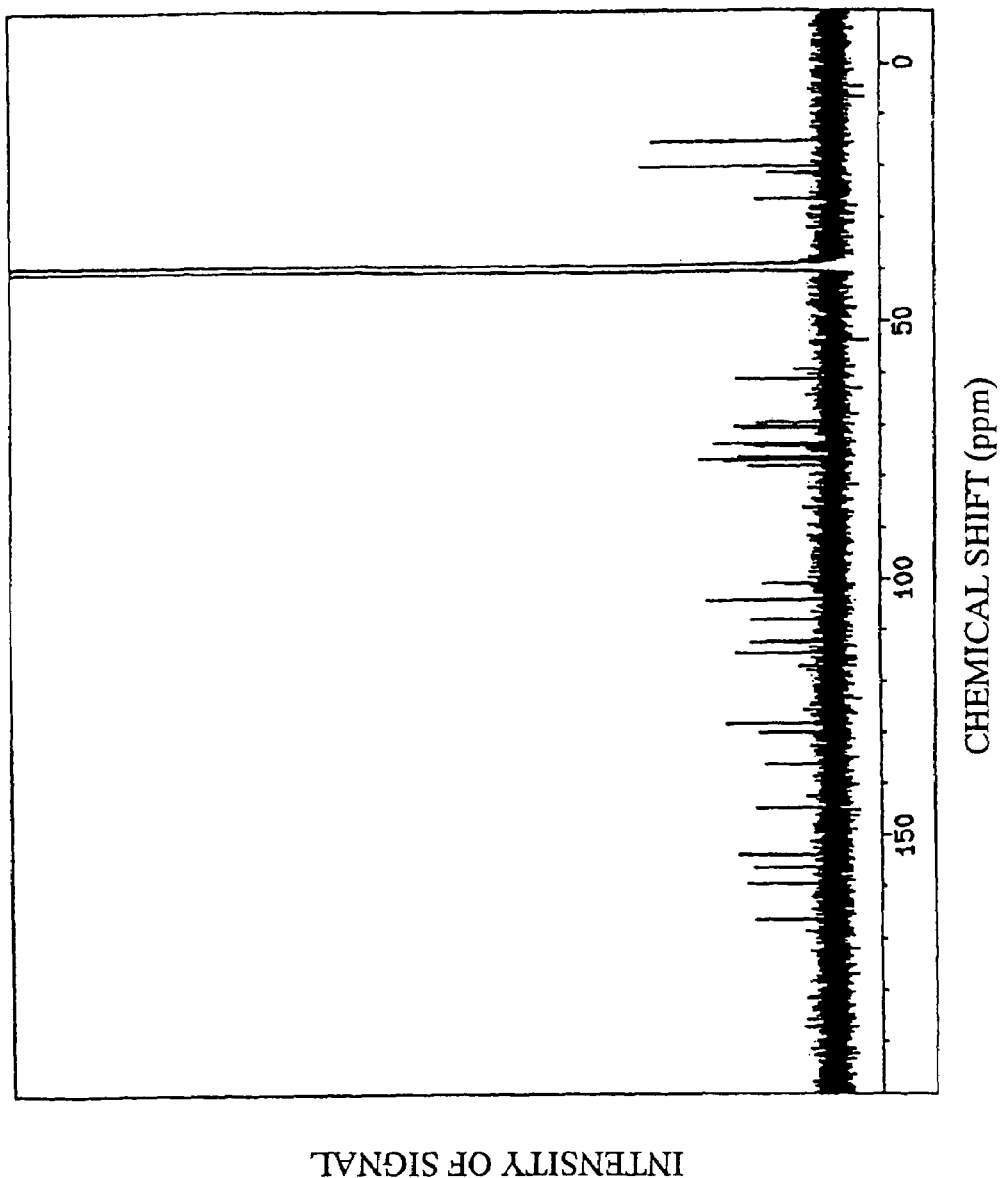
FIG. 14 is a chart showing $^{13}$C-NMR spectrum of the fraction 19/20-6 from root portions of Angelica keiskei koidz.

FIG. 14 shows $^{13}$C-NMR spectrum of the fraction 19/20-6 derived from root portions of *Angelica keiskei* koidz. In FIG. 14, the axis of abscissas is chemical shift (ppm), and the axis of ordinates is intensity of signal.

As a result of the analyses of the MS spectrum and NMR spectra for the fraction 19/20-6 derived from root portions of *Angelica keiskei* koidz., it was identified that the component is 4'-O-angeloyl-3'-O-[6-O-(β-D-glucopyranosyl)-β-D-glucopyranosyl]-khellactone (molecular weight: 668).

(2) The enhancing activity for NGF production of the fraction 19/20-6 derived from root portions of *Angelica keiskei* koidz. used as a sample, of which structure was identified in item (1) of Example 5, was determined in the same manner as in item (2) of Example 1. The sample was added so as to have the final concentration shown in Table 5. As a result, it was clarified that the fraction 19/20-6 derived from root portions of *Angelica keiskei* koidz., namely 4'-O-angeloyl-3'-O-[6-O-(β-D-glucopyranosyl)-β-D-glucopyranosyl]-khellactone, has an enhancing activity for NGF production. The results are shown in Table 5.

TABLE 5

| Fractionated Fraction (Detected Peaks: minutes) | Concentration (mg/ml) | Amount of NGF Produced (%) |
|---|---|---|
| Fraction 19/20-6 (18.8) | 1.00 | 337.7 |

(Here, the amount of NGF produced in the control was 0.063 ng/ml.)

Example 6

Enhancing Activity for NGF Production of 3-Hydroxy-8-[3-(4-hydroxyphenyl)-acryloyl]-5-methoxy-2-dimethyl chroman (1) The ethyl acetate extract obtained in item (1) of Preparation Example 1 was concentrated under a reduced pressure with a rotary evaporator, and thereafter the residue was dissolved in chloroform. The entire amount of the solution was adsorbed to silica gel BW-300SP (manufactured by Fuji Silysia Chemical Ltd.: 750 ml). Next, the absorbed substances were eluted stepwise with hexane:chloroform=2:5 (750 ml), chloroform (1000 ml), and chloroform:methanol=10:1 (1100 ml), and each of the eluted fractions was concentrated under reduced pressure to give each of silica gel fractionated fractions.

(2) The fraction eluted with chloroform:methanol=10:1 described in item (1) of Example 6 was dissolved in 30 ml in chloroform, out of which 15 ml was fractionated by using silica gel chromatography. The conditions therefor are given below. The silica gel used was BW-300SP (300 ml). The elution was carried out sequentially with chloroform (1800 ml) and chloroform:methanol=500:7 (300 ml) as developing solvents. Next, the elution was carried out with ethyl acetate (300 ml), and thereafter each of eluates was concentrated under reduced pressure to give each of silica column-fractionated fractions.

(3) The fraction eluted with ethyl acetate described in item (2) of Example 6 was dissolved in chloroform:methanol=50:1 (20 ml), and fractionated by using silica gel chromatography. The conditions therefor are given below. The silica gel used was BW-300SP (300 ml). A stepwise elution was carried out sequentially with chloroform:methanol=500:10 (1200 ml), chloroform:methanol=500:13 (500 ml), chloroform:methanol=500:19 (500 ml), chloroform:methanol=500:22 (800 ml) and ethyl acetate (500 ml) as developing solvents, and 18-ml aliquots per fraction were collected. Fraction Nos. 68 to 83 were collected from the resulting fraction and concentrated under reduced pressure, and each concentrate was dissolved in a 10% aqueous ethanol solution to give each of 10% aqueous ethanol solutions of the fractions 68 to 83.

(4) Each of the 10% aqueous ethanol solutions described in item (3) of Example 6 was fractionated by using reverse phase chromatography. The resin used was Cosmosil 140 C18-OPN (manufactured by Nakalai Tesque Inc., amount of resin: 50 ml). The elution was carried out by sequentially using 200 ml each of distilled water, a 10% aqueous ethanol solution, a 20% aqueous ethanol solution, a 30% aqueous ethanol solution, a 50% aqueous ethanol solution, and ethanol as developing solvents. Each eluted fraction was concentrated under reduced pressure, to prepare each fraction fractionated by Cosmosil.

(5) Thirty-six milligrams of a compound A was obtained from the fraction eluted with 30% aqueous ethanol solution of item (4) of Example 6 by recrystallization with ethyl acetate and hexane.

(6) The MS spectrum and the NMR spectra of the compound A prepared in item (5) of Example 6 were determined in the same manner as in item (2) of Example 2. The matrix used was m-nitrobenzyl alcohol. According to the mass spectroscopy, a peak of m/z 355 $(M+H)^+$ was detected.

The signals of NMR are shown below.

$^1$H-NMR: δ 1.25 (3H, s, 2-CH3), 1.32 (3H, s, 2-CH3), 2.47 (1H, dd, J=7.4, 17.2 Hz, 4-H), 2.83 (1H, dd, J=5.4, 17.2 Hz, 4-H), 3.70 (1H, m, 3-H), 3.85 (3H, s, 5-OCH3), 5.22 (1H, d, J=4.9 Hz, 3-OH), 6.65 (1H, d, J=8.7 Hz, 6-H), 6.84 (2H, d, J=8.6 Hz, 3"-H and 5"-H), 7.42 (1H, d, J=15.7 Hz, 2'-H), 7.46 (1H, d, J=15.7 Hz, 3'-H), 7.50 (1H, d, J=8.7 Hz, 7-H), 7.53 (2H, d, J=8.6 Hz, 2"-H and 6"-H), 10.02 (1H, s, 4"-OH)

$^{13}$C-NMR: δ 21.6 (2-CH3), 26.3 (2-CH3), 27.2 (4-C), 56.6 (5-OCH3), 67.8 (3-C), 78.5 (2-C), 103.4 (6-C), 110.0 (10-C), 116.8 (3"-C and 5"-C), 122.4 (8-C), 125.0 (2'-C), 126.9 (1"-C), 130.3 (7-C), 130.8 (2"-C and 6"-C), 141.9 (3'-C), 153.8 (9-C), 160.5 (4"-C), 161.5 (5-C), 190.4 (1'-C)

Here, in $^{13}$C-NMR, the sample was dissolved in deuterated dimethyl sulfoxide, and the chemical shift of the deuterated dimethyl sulfoxide was expressed as 2.50 ppm.

(7) As a result of the analyses of the MS spectrum and NMR spectra for the compound A, it was identified that the compound is 3-hydroxy-8-[3-(4-hydroxyphenyl)-acryloyl]-5-methoxy-2-dimethyl chroman (molecular weight: 354).

(8) The enhancing activity for NGF production of 3-hydroxy-8-[3-(4-hydroxyphenyl)-acryloyl]-5-methoxy-2-dimethyl chroman used as a sample, of which structure was identified in item (7) of Example 6, was determined in the same manner as in item (2) of Example 1. The sample was added so as to have the final concentration as shown in Table 6. As a result, it was clarified that 3-hydroxy-8-[3-(4-hydroxyphenyl)-acryloyl]-5-methoxy-2-dimethyl chroman has an enhancing activity for NGF production. The results are shown in Table 6.

TABLE 6

| Concentration (μM) | Amount of NGF Produced (%) |
|---|---|
| 200 | 457.7 |

(Here, the amount of NGF produced in the control was 0.668 ng/ml.)

INDUSTRIAL APPLICABILITY

According to the present invention, there is provided a medicament, a food, a beverage or a feed, each comprising a compound having a coumarin and/or chroman backbone, which is effective for the treatment or the like of a disease requiring enhancement of NGF production.

The medicament is useful as a therapeutic agent or prophylactic agent for a disease requiring enhancement of NGF production, such as a dementia or a nerve disorder. In addition, according to the present invention, there is provided an agent for enhancing NGF production comprising a compound having a coumarin and/or chroman backbone, and the agent is useful in functional studies on NGF and screening of a medicament for a disease associated with NGF.

In addition, the food or beverage effectively acts on amelioration of a symptom or the like of a disease requiring enhancement of NGF production by an intake as a daily foodstuff. Therefore, the foodstuff of the present invention comprising as an effective ingredient a compound having a coumarin and/or chroman backbone is a functional foodstuff which is effective for maintaining homeostasis of a living body.

The feed of the present invention can be contributed in maintaining homeostasis of a living body in an animal by an enhancing action of NGF production by its effective ingredient.

The invention claimed is:

1. A therapeutic agent or prophylactic agent for a disease requiring enhancement of nerve growth factor production, wherein the therapeutic agent or prophylactic agent comprises as an effective ingredient at least one isolated or purified compound selected from the group consisting of
   7-O-β-D-glucopyranosyloxy-8-prenyl coumarin,
   7-β-D-glucopyranosyloxy-6-prenyl coumarin,
   3'-O-β-D-glucopyranoyl khellactone,
   4'-O-angeloyl-3'-O-[6-O-(β-D-glucopyranosyl)-β-D-glucopyranosyl]-khellactone,
   a compound represented by the general formula (III):

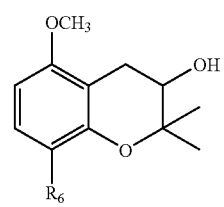

(III)

wherein $R_6$ is a hydrogen atom, hydroxyl group, carboxyl group, an aliphatic group, an aromatic group, an aromatic-aliphatic group or a saccharide residue, and pharmacologically acceptable salts thereof and optionally in combination with a pharmaceutically acceptable carrier.

2. The therapeutic agent or prophylactic agent according to claim 1, wherein the compound represented by the general formula (III) is
8-carboxyl-3-hydroxy-5-methoxy-2-dimethyl chroman or
3-hydroxy-8-[3-(4-hydroxyphenyl)-acryloyl]-5-methoxy-2-dimethyl chroman.

3. An enhancing agent for nerve growth factor production, wherein the agent comprises as an effective ingredient at least one isolated or purified compound selected from the group consisting of
7-O-β-D-glucopyranosyloxy-8-prenyl coumarin,
7-β-D-glucopyranosyloxy-6-prenyl coumarin,
3'-O-β-D-glucopyranoyl khellactone,
4'-O-angeloyl-3'-O-[6-O-(β-D-glucopyranosyl)-β-D-glucopyranosyl]-khellactone,
a compound represented by the general formula (III):

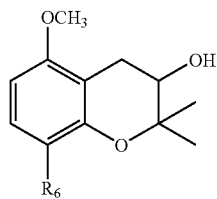

(III)

wherein $R_6$ is a hydrogen atom, hydroxyl group, carboxyl group, an aliphatic group, an aromatic group, an aromatic-aliphatic group or a saccharide residue, and pharmacologically acceptable salts thereof.

4. The agent according to claim 3, wherein the isolated or purified compound represented by the general formula (III) is 8-carboxyl-3-hydroxy-5-methoxy-2-dimethyl chroman or 3-hydroxy-8-[3-(4-hydroxyphenyl)-acryloyl]-5-methoxy-2-dimethyl chroman.

5. A food, beverage or feed for enhancing nerve growth factor production, wherein the food, beverage or feed comprises as an effective ingredient at least one isolated or purified compound selected from the group consisting of
7-O-β-D-glucopyranosyloxy-8-prenyl coumarin,
7-β-D-glucopyranosyloxy-6-prenyl coumarin,
3'-O-β-D-glucopyranoyl khellactone,
4'-O-angeloyl-3'-O-[6-O-(β-D-glucopyranosyl)-β-D-glucopyranosyl]-khellactone,
a compound having a 2-dimethyl chroman backbone, and pharmacologically acceptable salts thereof.

6. The food, beverage or feed according to claim 5, wherein the isolated or purified compound having a 2-dimethyl chroman backbone is the compound represented by the general formula (III):

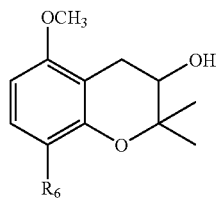

(III)

wherein $R_6$ is a hydrogen atom, hydroxyl group, carboxyl group, an aliphatic group, an aromatic group, an aromatic-aliphatic group or a saccharide residue.

7. The food, beverage or feed according to claim 6, wherein the isolated or purified compound represented by the general formula (III) is
8-carboxyl-3-hydroxy-5-methoxy-2-dimethyl chroman or
3-hydroxy-8-[3-(4-hydroxyphenyl)-acryloyl]-5-methoxy-2-dimethyl chroman.

8. Isolated or purified 7-β-D-glucopyranosyloxy-6-prenyl coumarin or a salt thereof.

9. Isolated or purified 4'-O-angeloyl-3'-O-[6-O-(β-D-glucopyranosyl)-β-D-glucopyranosyl]-khellactone or a salt thereof.

10. Isolated or purified 8-carboxyl-3-hydroxy-5-methoxy-2-dimethyl chroman or a salt thereof.

11. A method for enhancing nerve growth factor production, said method comprising:
administering to an animal, as an effective ingredient, at least one isolated or purified compound selected from the group consisting of
7-O-β-D-glucopyranosyloxy-8-prenyl coumarin,
7-β-D-glucopyranosyloxy-6-prenyl coumarin,
3'-O-β-D-glucopyranoyl khellactone.
4'-O-angeloyl-3'-O-[6-O-(β-D-glucopyranosyl)-β-D-glucopyranosyl]-khellactone,
a compound represented by the general formula (III):

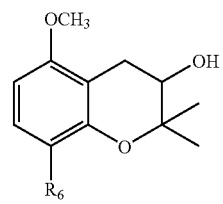

(III)

wherein $R_6$ is a hydrogen atom, hydroxyl group, carboxyl group, an aliphatic group, an aromatic group, an aromatic-aliphatic group or a saccharide residue,
and pharmacologically acceptable salts thereof.

12. The method according to claim 11, wherein the compound represented by general formula (III) is

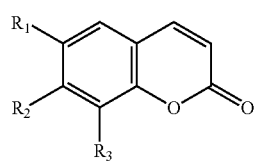

(I)

8-carboxyl-3-hydroxy-5-methoxy-2-dimethyl chroman or
3-hydroxy-8-[3-(4-hydroxyphenyl)-acryloyl]-5-methoxy-2-dimethyl chroman.

* * * * *